(12) United States Patent
Satapathy et al.

(10) Patent No.: US 11,594,313 B1
(45) Date of Patent: Feb. 28, 2023

(54) SYSTEM, APPARATUS AND METHOD FOR AUTOMATED MEDICATION ADHERENCE IMPROVEMENT

(71) Applicant: INTELLIGENT AUTOMATION, LLC, Rockville, MD (US)

(72) Inventors: Goutam Satapathy, Bethesda, MD (US); Thomas Wavering, Ashburn, VA (US); Jyotirmaya Nanda, Gaithersburg, MD (US); Lisa Holt, Silver Spring, MD (US); Alexander Grushin, Rockville, MD (US)

(73) Assignee: INTELLIGENT AUTOMATION, LLC, Rockville, MD (US)

( * ) Notice: Subject to any disclaimer, the term of this patent is extended or adjusted under 35 U.S.C. 154(b) by 226 days.

(21) Appl. No.: 16/844,394

(22) Filed: Apr. 9, 2020

Related U.S. Application Data

(63) Continuation-in-part of application No. 15/181,504, filed on Jun. 14, 2016, now abandoned.

(51) Int. Cl.
| | |
|---|---|
| *G16H 20/10* | (2018.01) |
| *G16H 40/67* | (2018.01) |
| *G16H 50/70* | (2018.01) |
| *A61J 7/04* | (2006.01) |
| *G16H 10/20* | (2018.01) |

(52) U.S. Cl.
CPC .............. *G16H 20/10* (2018.01); *A61J 7/04* (2013.01); *G16H 10/20* (2018.01); *G16H 40/67* (2018.01); *G16H 50/70* (2018.01); *A61J 2200/30* (2013.01); *A61J 2205/70* (2013.01)

(58) Field of Classification Search
None
See application file for complete search history.

(56) References Cited

U.S. PATENT DOCUMENTS

| | | | | |
|---|---|---|---|---|
| 2012/0316897 A1* | 12/2012 | Hanina | .................. | G16H 20/10 705/3 |
| 2013/0169781 A1* | 7/2013 | Hanina | .................. | G16H 30/40 348/77 |

FOREIGN PATENT DOCUMENTS

WO   WO-2007138489 A2 *  12/2007  ......... G06F 19/3418

* cited by examiner

*Primary Examiner* — John A Pauls
(74) *Attorney, Agent, or Firm* — Amster, Rothstein & Ebenstein LLP

(57) ABSTRACT

Computer and mobile device-based systems and computer-implemented methods are described for automated medication adherence improvement for patients in medication-assisted treatments. The computer and mobile device-based systems includes modules and components to help patients in identifying prescribed medications, logging medication events, and to provide patients with personalized and targeted adherence enhancing interventions consisting of short questions, tips, advices, suggestions, strategies etc. by applying data mining and statistical analysis techniques on the individual and population-level data collected primarily from the same system.

22 Claims, 16 Drawing Sheets

4112 Palm as a container for 4111

4113 Pill box cap as a container for 4111

SYSTEM, APPARATUS AND METHOD FOR AUTOMATED MEDICATION ADHERENCE IMPROVEMENT

BACKGROUND OF THE INVENTION

This application claims priority to and is a Continuation-In-Part application of nonprovisional U.S. patent application Ser. No. 15/181,504 filed on Jun. 14, 2016, the complete disclosure of which is incorporated by reference herein.

This invention was made with government support under Contract No. NIH/NIDA N44DA-14-2236 awarded by the National Institute of Health, National Institute on Drug Abuse. The government has certain rights in the invention.

This invention relates to a system that assists patients to take prescription medications, engage in self-evaluation of device-prompted questions related to personal adherence barriers, receive personalized suggestions, tips, advices, and strategies to overcome barriers with a goal to track and improve adherence, including tools to track the application of those suggestions, tips, advices, and strategies to help and discover the strategies that helps the patient most using user end software applications and mobile computing devices such as smartphones, tablets and wearables (e.g., smart watches, smart glasses with augmented reality, smart neck wears).

It is believed that poor medication adherence accounts for billions of dollars in healthcare costs in the form of additional treatments that are required because patients have failed to take needed medication. There are a number of reasons why a particular individual may not be taking his or her medication as prescribed. A number of research studies have been conducted to determine major and minor, primary and secondary and other categories (such as by percentage) of adherence barriers of a sample population receiving a particular treatment such as specific type of lung cancer, diabetes, mental health conditions, and others. However, given an individual receiving a medication treatment there is no way to assess or predict why he or she may not take medications as prescribed during the course of the treatment.

Multiple types of factors or barriers affect why an individual does not take medication as prescribed. Some are intentional barriers resulting from individual's misperception on medication affordability, benefits (e.g., this medication is not needed at all or any longer), and adverse effect concerns (e.g., methadone rots my teeth). Research also shows those intentional barriers are sometimes associated with or lead to patient's unintentional barriers such as forgetfulness. Other barriers include lack of access to medical professional or social support to discuss medication errors and treatment details (such as smoking cessation, or HIV infection prevention). In some cases, comorbidity of drug & smoking addiction and psychiatric disorder (e.g., schizophrenia, depression, mood, attention-deficit/hyperactivity disorder) also play a role in low adherence. Psychosocial behavior becomes a factor in the low adherence seen among patients with comorbid disorder. Also, among certain section of population low cognitive skill also contributes to poor adherence. The percentage of non-adherence cases attributed by a type of barrier is analyzed in a case study by case study (e.g., using clinical, non-clinical, observational, electronic pill tracking devices and programs, or community surveys) basis involving a segment of population receiving a study-specified type of treatment. These are post-study analysis findings that are used for population modeling and stratification (i.e., subgrouping based on the patient profile) and designing intervention campaign for patients in within a group or sub-group receiving a specific type of treatment.

To improve medication adherence, various types of interventions, called Adherence Enhancing Intervention (AEI) are applied. Educational intervention campaign includes providing textual, graphical, and multimedia information through appropriate medium for the patient to understand and learn techniques on what to do and how to improve adherence. Financial incentives (or disincentives) such as cashback, service discount, coupons, vouchers, gift cards, and tickets for either materialistic and entertainment value is another form of intervention. Medication reminder service via telephone, phone text messaging, pharmacy or non-pharmacy apps with medication dose and refill reminders, and wireless or Internet-connected pill bottles (including boxes, trays, or dispensing systems) with built-in sensors are another type of intervention. Educational campaign and medication reminder are the popular forms of AEI in many adherence improvement programs.

The post-study analysis findings and models are used to develop educational campaigns, called educational interventions to improve the community-wide and treatment-specific adherence to medication. These interventions, in the form of electronic (e.g., emails, text messages, websites, social media, TV and smartphone infomercials), and non-electronic (i.e., paper, pamphlets, brochures, magazines) medium or channels have been used to influence individual's adherence behavior. However, these are non-targeted means of improving adherence. For example, a patient whose primary barriers to adherence are about lack of belief on the medication may not benefit from receiving information about medication organization.

Traditionally, to make adherence improvement a targeted process, which would conceivably make it more effective, various healthcare programs such as medication therapy management (MTM) have been developed in which medical providers such as pharmacists and physician's office offer periodic or regular counseling services to improve patient's medication adherence. These individualized or group counseling sessions are designed to engage patient in question-answer sessions, and listening to and receiving information with advices and suggestions on improving adherence. The voluntary and participating patients also bring in with them their own assessments of the treatment progress, often called medical diary to such sessions. MTM is an expensive process, yet can produce reasonable improvement with targeted and focused counseling-based interventions than community-wide and treatment-specific educational campaigns.

However, during the treatment progress, or even from the start of medication, there are no clear and automated mechanisms to collect and analyze the likely factors that may contribute to an individual's lack of adherence, or poorer adherence without involving human capital. Without such automated data collection and analysis mechanism, automated delivery of targeted or personalized interventions cannot be scaled. MTM suffers from such scalability as it becomes more expensive to engage large segments of population.

Beside the issue with the scale of the human capital-based adherence improvement programs, there is also the issue of intervening at the right time with the right message of advice and suggestions to have an effective impact of the intervention. In other words, unless the periodic visits with medical professionals are scheduled frequently (e.g., daily), it may become too late to discover the barriers that a patient experienced or was experiencing and consequently too late to offer any effective intervention messages. One example of such cases is patient experiencing medication side effects and patient receiving right set of coping strategies when they experience. A frequent visit for counselling is a challenge for the patient, and it makes the program further expensive as well.

With available mobile devices such as smartphones and wearables, popular types of interventions such as educational and medication reminders are now delivered effectively. However, no system has been developed to use mobile device only to monitor, assess and predict a patient's adherence behavior in an automated manner and use that information to deliver personalized targeted educational interventions in an automated manner. For example, there are many wireless or Internet-connected pill storage system (e.g., bottles, bottle caps, boxes, trays, or dispensing systems) with built-in sensors exist that can monitor and keep track of patient taking pills from the system, and thus be able calculate adherence score, and used to provide educational intervention via the mobile devices. However, such system will require patient to use two platforms—pill storage and mobile device. Similarly, there exist systems that can potentially use mobile device optical sensors such as a camera to potentially identify pill that patient is about to take and also monitor the activity of the patient taking the same medication, and use this information to assess patient's adherence; however no mobile computing device-based system exists that uses monitored adherence information from the mobile device to provide automated intervention to the patient consisting of the actions they can take and strategies they can follow intended to changing their behavior.

Most importantly, there does not exist any mobile computing device-based system that engages patients in an automated self-evaluation of their present and eminent barriers that the patient may be encountering, even prior to the patient showing the symptoms of non-adherence by not taking medication as prescribed, and then using the self-evaluation result to personalize the educational information to the target patient. In other words, there are no mobile device-based systems that provide automated preemptive and targeted interventions consisting of strategies that the patient can practice and learn (e.g., keeping medications at two places where the patient most of the time so that he or she does not forget scheduled doses), discover and apply alternative methods to overcoming barriers (e.g., following alternative means of managing nausea side effects), and resources to where patient can be directed to discuss and learn (e.g., specific social media, web sites, and forums).

Finally, no such mobile device-based system exists that not only provides for a patient to track adherence, learn personal adherence barriers and improve adherence by putting personalized suggestions and advices into practice, but also provides high resolution behavioral data to the medical professionals, such as those involved in MTM programs to further fine tune and target their program-offered interventions, cut down cost escalation, and make the program scalable and affordable to large population.

SUMMARY OF THE INVENTION

In accordance with the present invention, the apparatus, system and method are embodied into a system called automated medication adherence improvement system 1000 as described in FIG. 1. The apparatus, system and method are intended to be used by the patients and medication adherence service providers. The invention consists of a user-end software application, computer executable instructions 4500 to be used on a user-end apparatus or system, which is a mobile computing device with a software application, intended to be used by the patient and a back-end processing system 2000, a set of computer executable instructions often called as cloud-based system or big data analytics platform, intended to be used by medication adherence service providers. In accordance with the invention, the two systems are communicatively coupled over a communication medium such that the back-end processing system, once set up, can operate autonomously to predict, assess, estimate, calculate, or measure a patients medication adherence and adherence barriers by virtue of patient using the software application 4500, and intervene the patient via the user-end software application 4500 with personalized notifications, questionnaires and messages with intention to change their behavior, learn strategies to overcome and manage the barriers in order to improve their medication adherence measures. The invention includes couplings or connectivity provided by the back-end processing system for the third-party or external service provider systems 3000 to communicate with the system 1000.

In some embodiments, a medication adherence service provider may be defined as an individual or organization who is a stakeholder to ensuring patients medication adherence is improved, and by that definition the service provider can be doctors, medical practitioners, primary care physicians, nurses, nursing homes, physician's office, hospitals, pharmacies, health insurers, payer, PBMs, pharmaceuticals, caretakers, family members, and including patients themselves. A medication service provider is the one who authorizes and sets various system and user level parameters for a patient to use the user-end apparatus and software application, sets the prescription details, tracks and monitors patients behavior including medication events, responses to (service provider or system-) prompted intervention messages, their feedback and experiences from taking (or not taking) medications, and communicates with the user-end apparatus via the back-end processing system.

In accordance with the invention, the patient uses the user-end software application to manage his or her medication schedules in accordance with the authorized prescription input by the service provider. The system 1000 allows prescriptions to be updated, modified, extended, or changed by service provider only and the system 1000 allows the patient to change or adapt his or her medication schedule as per the latest prescription data.

In accordance with the invention, the system 1000 allows the patient to record a medication event via the user-end apparatus or system by providing a series of instructions to take prescribed medication. In accordance with the invention, based on the system and user-level parameters set by the service provider in the back-end processing system, the set of activities to be followed by the patient may vary. The activities at the minimum include showing a single pill or multiple pills on the palm of the hand, on the pill bottle cap, or any flat surface container with optically visible reference marks to the optical sensors on the mobile device. In this minimum set of activity, called pill identification activity, the user-end apparatus or system records and stores the images in the memory (non-transitory storage medium) and uses video and image processing techniques on them to identify the pill. In accordance with the invention, the user-end apparatus or system extract features from the video and compares them with predefined or iteratively-adjusted set of parameters to identify the pill. The other activities may include showing the pill or pills in the mouth by opening the mouth, swallowing the pill and then showing the empty mouth, and uttering a few words for verification of swallowing. In accordance with the invention, the user-end software application 4500 provides real-time feedback to the patient of successful or unsuccessful recording the medication event. In accordance with the invention, a medication event has been successfully completed, if the user-end software application has successfully identified the medication, number of medication (i.e., dose amount), and dose schedule (i.e., twice a day, or one in the morning and one at the bedtime) as per the prescription. In accordance with the invention, a medication event is centered on taking the right medication as prescribed instead of merely the right way of administering the medication.

In accordance with the invention, use of optical sensors on the mobile devices to log medication event increases accuracy of the medication event log by ensuring that the medication to be taken by the patient matches with the prescribed medication, that is, matches the type of medication, number of medications, and timing of the medication. In accordance with the invention, accuracy of the medication event log leads to accuracy of patient-level adherence measures.

In accordance with the invention, the system 1000 also allows the patient to record a medication event, by entering the details of medication information data via the user-end software application. This manual entry of medication event data is a failure-safe contingency in the medication event recording method or process, where failure could occur because of technical reasons, and human behavior and schedule reasons.

In accordance with the invention, the system 1000 prompts, notifies, or provides visual and auditory indicators to the patient via the user-end apparatus or system, or software application when it is time for the patient to take medications. The system uses the prescription information and recorded medication events to guide the patient to take the pill or pills at the time of medication event recording that is conformant to the prescription.

In accordance with the invention, the system 1000 prompts, notifies, or provides visual and auditory indicators to the patient via the user-end apparatus or system, or software application when there are new intervention messages ready for the patients. In this invention, an intervention message is a set of instruction-guided interactions of the patient with the mobile device. An intervention message can be a set of questions prompted from the mobile device that patient may answer, or activities that patient may perform that may or may not be monitored using the sensors (such as camera, touch, proximity, accelerometer, gyroscope, barometer, GPS, WiFi, Bluetooth, near field, cellular, ambient light) on the user-end apparatus such that the recorded or tracked answers and activities are combined with visual and auditory feedbacks. Visual feedbacks may consist of text, graphics, pictorial, video, or combination there-of presented on the devices display medium. The data collected from sensors or user inputs through mobile device interactions (e.g., entering text or dictations, or movement) are collected by the user-end apparatus or system as the patient's intervention engagement data. Examples of intervention engagement data may include answers to a question such as if "the patient has skipped doses in the past", or time taken in reading descriptions explaining nausea side effects and instructions on how to manage it. The intervention engagement data are available for display on the user-end apparatus or system to the patient upon the patients request In accordance with the invention, the system 1000 allows the patient via the user-end software application 4500 to record their own experiences with medications without being prompted. The experiences include feedback on medication schedules, current and new personal barriers to taking medication, side effects they are experiencing, the side-effect coping strategy or remedial actions they are following, and effectiveness of the side effect coping strategies they have been following. These experiences called medication experience data are recorded via the user-end apparatus or system as text input (e.g., touch screen or keyboard input), multiple choice or checkboxes answers, or voice dictation. The medication experience data are available for display on the user-end apparatus or system to the patient upon the patients request.

In this invention, the medication event data, intervention engagement data and medication experience data collected from the user-end apparatus or system is called patient data. In this invention, patient data is collected from single or single set of communicatively coupled devices, and use to both assess, monitor, and track adherence, as well as to provide tips, advices, suggestion and directives to improve adherence.

In accordance with the invention, the patient data storage module of the back-end processing system 2000 collects the patient data from each user-end apparatus or system, parses and processes them and stores them. The metrics calculator module of the back-end processing system at specific times, set as system level parameters by the service provider, calculates the various types of metrics for each patients such as various types of adherence score, engagement level scores, and medication experience scores for each patient and for various groups and subgroups of patients set by the service provider from the service provider-end apparatus or system. The intervention delivery module of the back-end processing system applies data mining and pattern matching, and adherence risk calculation algorithms to the patient data and metrics to determine the further intervention messages that may be prompted to each patient. The delivery module constructs the intervention messages, controls the volume, length, or number of intervention messages, and also controls delivery frequency or timing of the intervention messages for each patient. The notification delivery module of the back-end processing system keeps track of the metadata such as timestamp, and type of data associated with the patient data, and applies time series pattern matching algorithms to construct notification messages, and send the notification messages using the user-end apparatus or system about the deficiency or discrepancy in the patient data. Examples of discrepancy data include lack of patients' engagement with the intervention messages. The notifications are delivered in the form of emails, short text messages, instant messages via third-party instant messaging applications, multimedia messages, automated phone calls, smartphone notification messaging system, and in-app notifications.

In accordance with the invention, the patient data and metrics data are available to the service provider from the data storage and computing system via a service provider-end apparatus or system. The examples of service provider-end apparatus or system are Internet browser-based applications, desktop applications, database or cloud-based applications, or mobile applications with a graphical user interface to display the patient data and metrics data.

In accordance with the intervention, the service provider uses service provider-end apparatus or system and notification delivery module of the back-end processing system to construct notification messages using message templates and send the service provider-constructed messages to a patient or group of patients.

BRIEF DESCRIPTION OF THE FIGURES

The above-mentioned and other features and objects of this invention and the manner of obtaining them will become more apparent, and the invention itself will be better understood by reference to the following description of embodiments of the present invention taken in conjunction with the accompanying photo, wherein.

DETAILED DESCRIPTION OF EMBODIMENTS OF THE INVENTION

For the purpose of promoting an understanding of the principles of the invention, reference will now be made to the embodiments illustrated in the figures, which are described below. It will nevertheless be understood that no limitation of the scope of the invention is thereby intended. The invention includes any alterations and further modifications in the illustrated devices and described methods and further applications of the principles of the invention, which would normally occur to one skilled in the art to which the invention relates.

In some embodiments, the systems and methods described herein are intended for use by patient with the goal that patient's adherence is predicted, assessed, estimated, calculated, or measured by virtue of patient using the software application 4500 and following the method, and the system uses the predicted, assessed, estimated, calculated, or measured information to provide interventions and notification messages automatically without requiring service provider's assistance.

Figure 1:
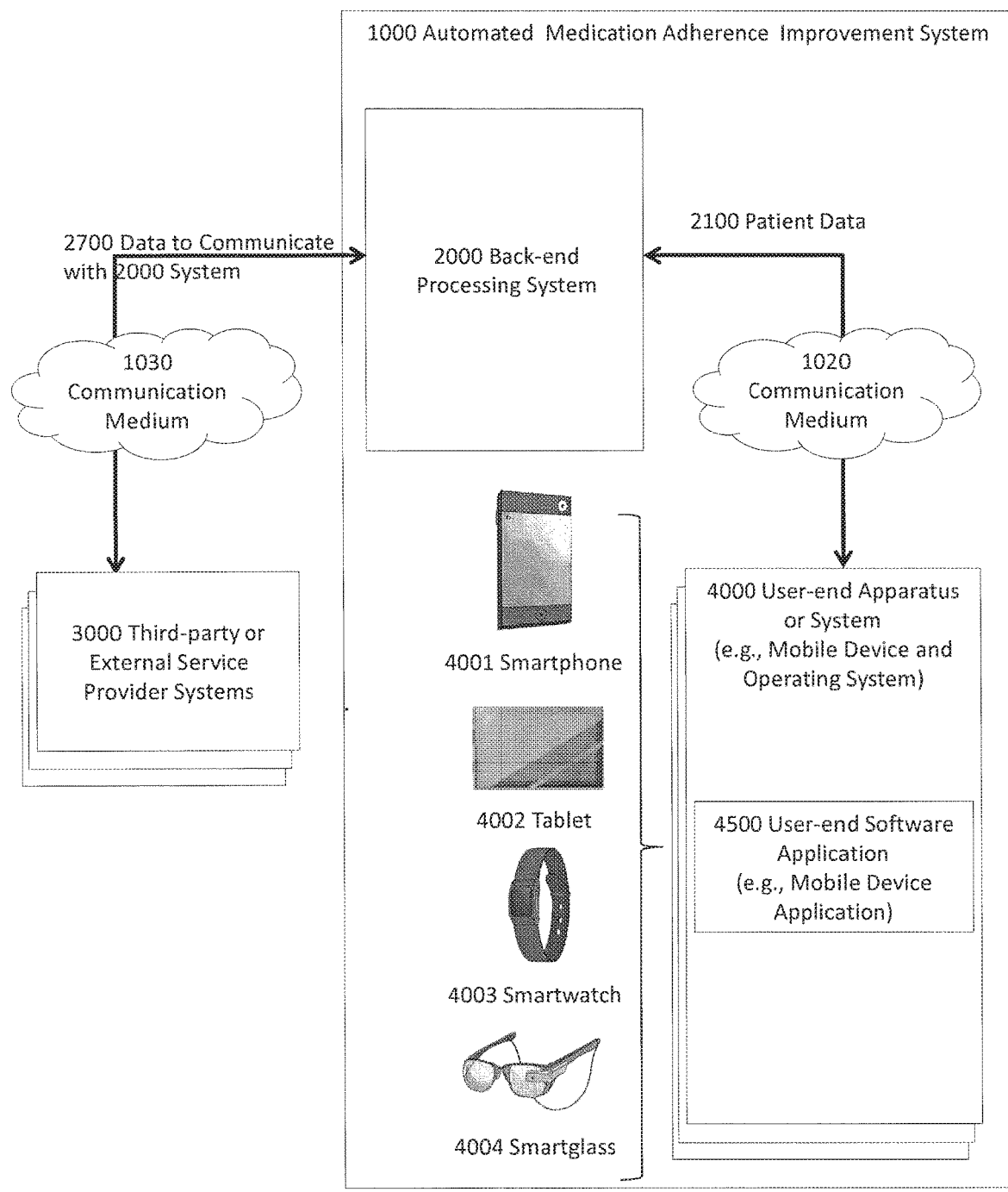
FIG. 1 describes different sub-systems of automated medication adherence system that are communicatively coupled in accordance with an embodiment of the present invention.

In accordance with the invention as illustrated in FIG. 1, the automated medication adherence improvement system 1000 consists of two systems that are communicatively coupled—a back-end processing system 2000 and an user-end apparatus or system 4000 within which a user-end software application, a set of computer executable instructions, 4500 is collocated. In some embodiments, the communication medium 1020 may refer to cellular, LTE, Wi-Fi, Ethernet, LAN, WAN, Internet, USB, Bluetooth Communication Systems. In some embodiments, a user-end apparatus or system may refer to a mobile device with an operating system such as smartphone 4001, tablets 4002, smartwatches 4003 and smart glasses 4004. In some embodiments, the user-end software application 4500 may physically exist on combination of communicatively coupled mobile devices. For example, application 4500 may be located on both smartphone and smart watch that are communicatively coupled. In some embodiments, user-end software application 4500 may be communicatively coupled with other applications that are physically collocated with the user-end end apparatus or system. For example, application 4500 may work with a Facebook™ Messenger Platform—a third party application that offers messaging services on mobile device, to provide some of the functionalities of 4500 (illustrated in FIG. 3).

In accordance with the invention as illustrated in FIG. 1, the automated medication adherence improvement system 1000 is communicatively coupled with third part or external service provider systems for the automated medication adherence improvement system and method to operate as described in this invention. In some embodiments, the medication adherence service provider provide 2700 data that may include patient enrollment data, prescription data, medication label data, other authorization and security configuration data, etc. to the system 2000 via the system 3000. In some embodiments, the communication medium 1030 may refer to cellular, LTE, Wi-Fi, Ethernet, LAN, Internet, USB, Bluetooth communication systems.

Figure 14:
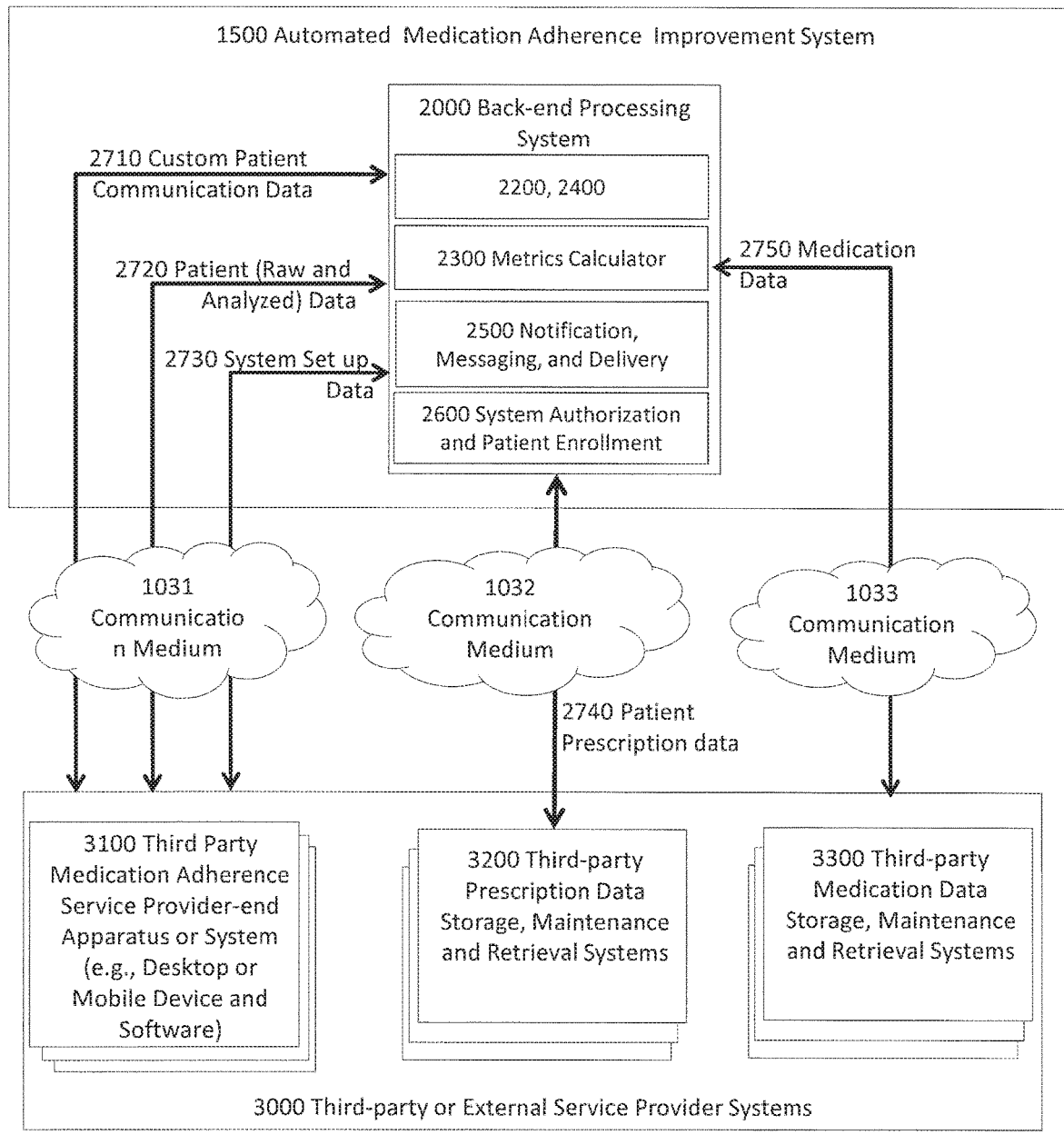
FIG. 14 describes the details of communication with the third-party systems with the back-end processing system in accordance with an embodiment of the present invention.

In some embodiments as illustrated in FIG. 1, the back-end processing system 2000 is intended for use by only authorized and registered patients, where authorization and registry information is provided by a service provider so that it is the service provider's responsibility to verify the accuracy and validity of the prescription that the patient needs to adhere as well as authenticity of the patient as the individual to who the prescription is issued. In some embodiments as illustrated in FIG. 14, the patient's prescription information entered into back-end processing system 2000 occurs via service provider-end apparatus 3100, or communicatively coupled third party systems 3200 that maintain the authorized prescription and specify the communication medium 1032 or interface using which prescription information for a patient are retrieved. In accordance with the invention, authorization and authenticity of the patient and prescription is critical in this invention because prescription is the basis against which patient's adherence is predicted, assessed, estimated, calculated, or measured, and improved.

Figure 2:
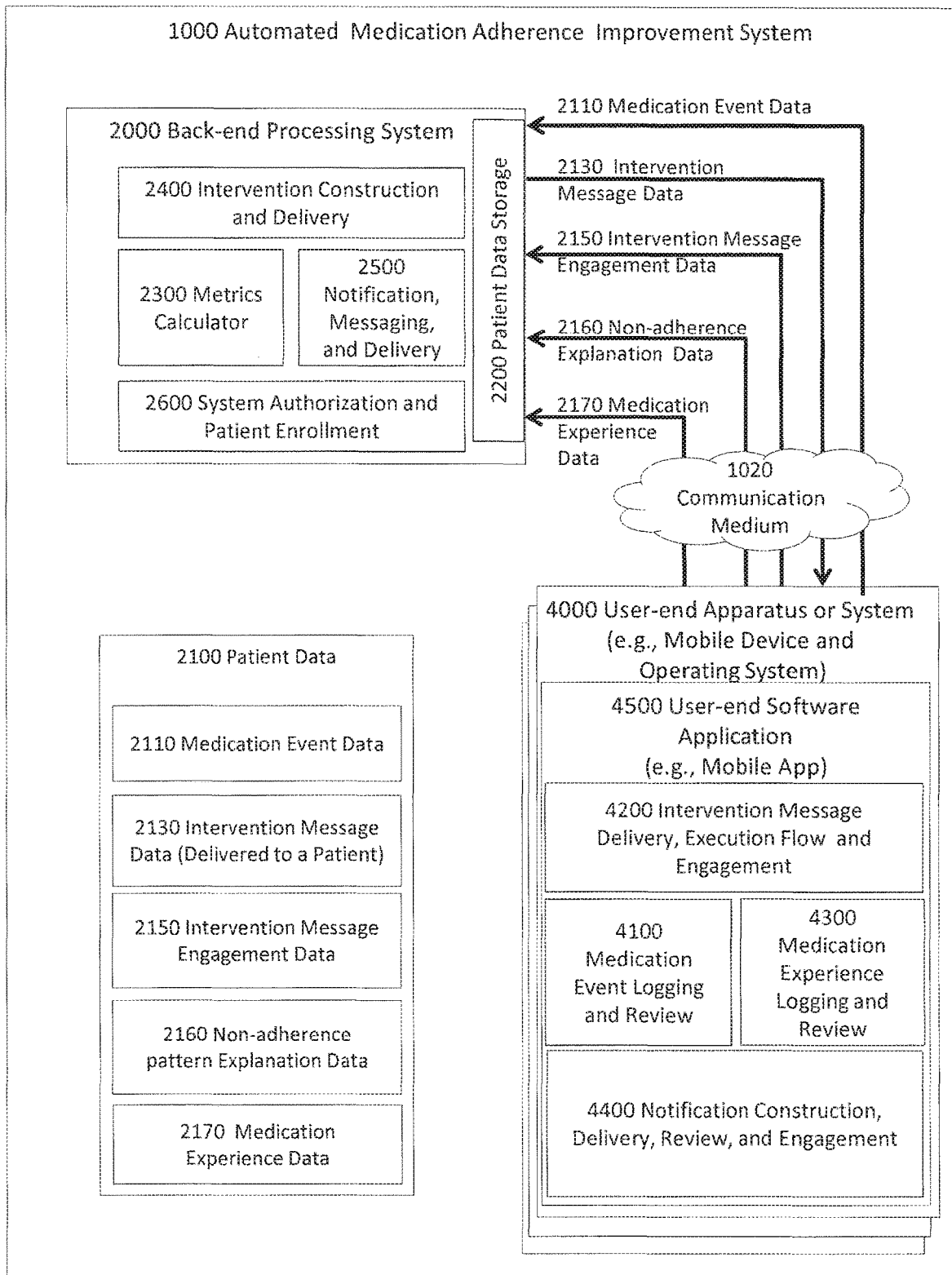
FIG. 2 describes details of components of each sub-system of automated medication adherence system in accordance with an embodiment of the present invention.

In accordance with the invention, user-end apparatus or system 4000 is a system of systems, or combinations of systems and apparatus that are communicatively coupled or integrated to enable the user-end software application 4500 to operate. In some embodiments, the user-end software application refers to a mobile app. In some embodiments, the user-end software application may also refer to a messenger bot. In accordance with the invention, the application 4500 provides two key functionalities—medication event and experience logging and review, and intervention message and notification delivery (to the patient), review and engagement. In accordance with this invention, FIG. 2 illustrates key modules of user-end software application 4500 that enables the functionalities, namely, medication event logging and review 4100, intervention message execution flow and engagement 4200, medication experience logging and review 4300, and notification construction, delivery, review and engagement 4400. In some embodiments, these functionalities are enabled by mobile app, messenger bot, or both.

Figure 3:
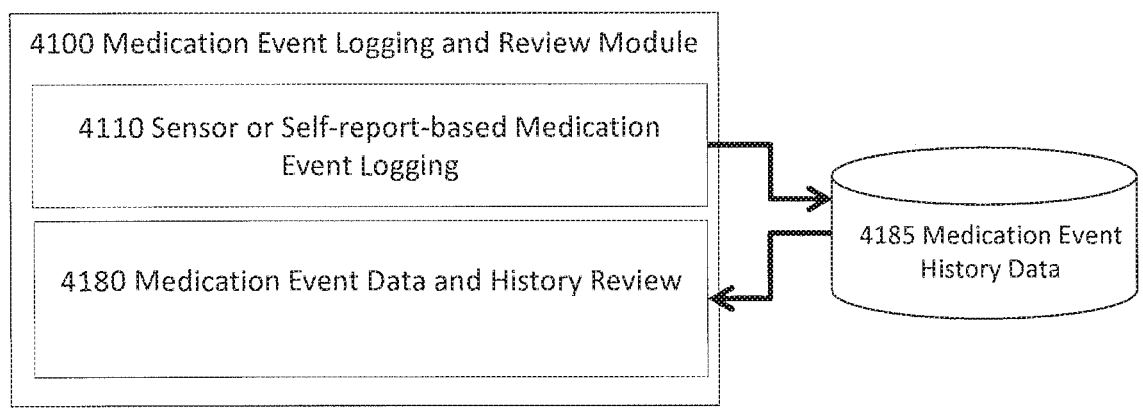
FIG. 3 describes details of medication event logging and review module in accordance with an embodiment of the present invention.

FIG. 3 illustrates two components of medication event logging and review 4100 module in accordance with the invention, namely, sensor or self-report-based medication event logging 4110 and medication event data and history review 4180. In accordance with the invention, the 4110 component creates and stores the medication event outcome measures 4181 (illustrated in FIG. 4) into medication event history data storage system 4185. In some embodiments, the medication event history data storage system 4185 is included in both user-end apparatus or system and back-end processing system in the form of non-transitory computer readable storage medium. In accordance with the invention, 4180 components retrieve the medication event data and history from 4185 and present the event history data to the patient along with the feedback about non-adherence patterns and questions to explain the patterns.

Figure 4:
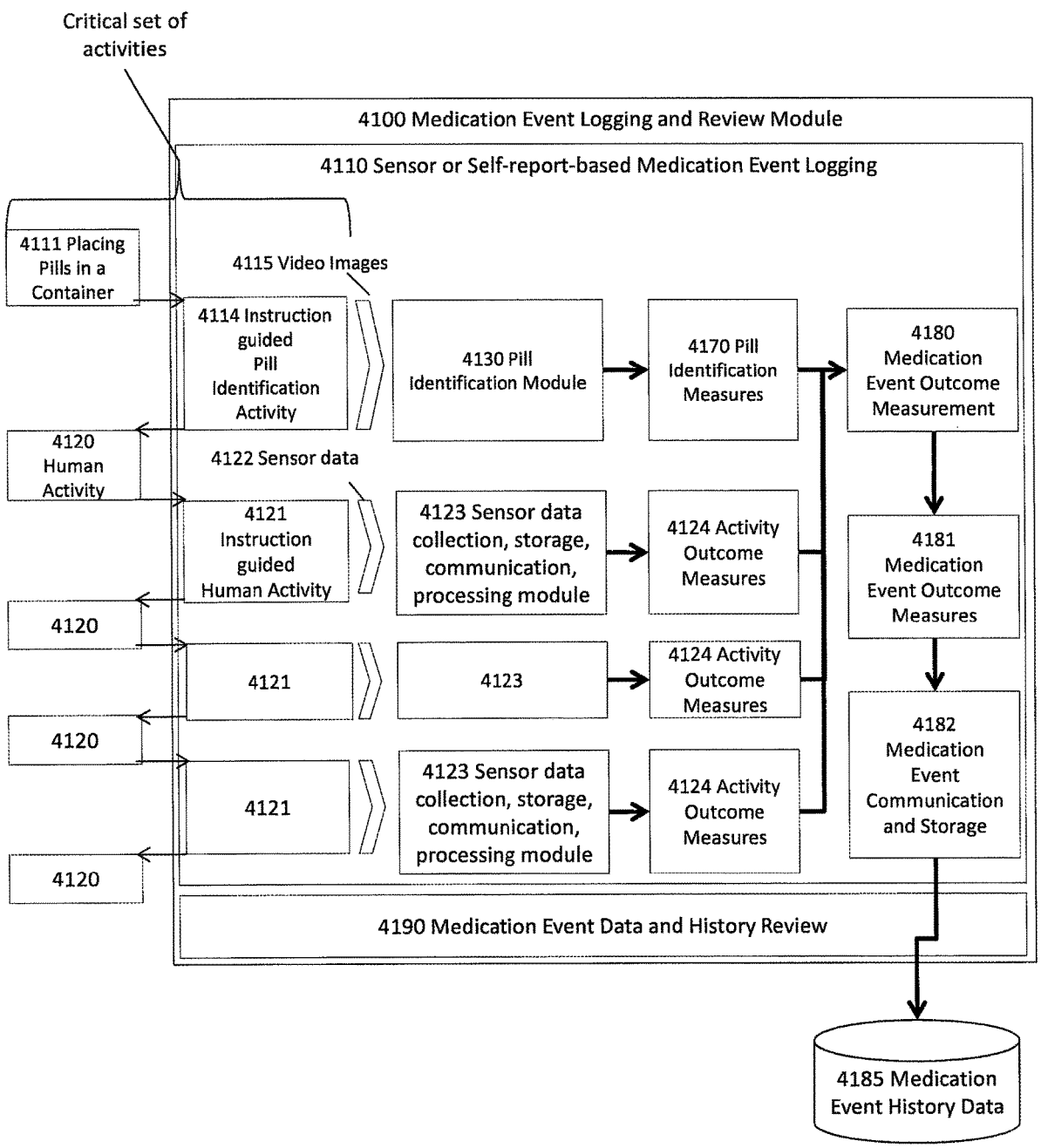
FIG. 4 describes the details of sensor or self-report-based medication event logging process in accordance with an embodiment of the present invention.

FIG. 4 illustrates the definition of medication event logging process, in accordance with the invention. An individual performs various activities (4111, 4120 in FIG. 4) defined by the system and set by the service provider for the individual, but only demonstrates the activities (4115, 4122 in FIG. 4) to the mobile device sensor such as camera or microphone only what is instructed to him or her via the mobile device's display or audio output. Showing pill as a target on a container to the mobile device camera as user-end apparatus starts processing the video acquired from the camera is one example of such instructions for pill identification activity. Showing pill as a target on the mouth to the mobile device camera as user-end apparatus starts processing the video acquired from the camera is another example of such instructions for pill taking activity. Showing empty mouth as a target to the mobile device camera as user-end apparatus starts processing the video acquired from the camera is another example of such instructions for pill swallowing activity. Speaking few words or sentences to the mobile device microphone as user-end apparatus starts processing the audio acquired from the microphone is another example of such instructions for pill swallowing activity. In accordance with the invention, each demonstration of the system-instructed activity by the patient is sensed by the mobile device sensors to generate sensor data 4122 and requires application of mobile device sensor data acquisition, collection, storage, communication, and processing 4123 such as image or computer vision processing, acoustic signal processing, voice recognition and analysis, or text analysis to determine the activity outcome measures 4124. For example, pill identification activity 4114 is sensed and acquired as video images 4115 and processed by pill identification component 4130 to calculate (positive or negative) pill identification outcome measures 4170, which includes but not limited to number of times pill identified during the activity, probability distribution of pill identification, duration of the activity, timestamps of the activity, and others image processing measures. The combination of outcome measures of all mobile device instructed activities results in determination of medication event outcome measure 4181, which is determined by the medication event measurement component 4180. In some embodiments, in accordance with the invention, the medication event outcome measure 4181 is presented to the patient via the mobile device display so that individual may be requested to repeat the activities, if possible and as needed per the system parameters set in the back-end processing system by the service provider.

In accordance with the invention, FIG. 4 illustrates pill identification activity as the critical set of activities performed by the patient, where upon the patient prepares for pill identification activity by placing the pill or plurality of pill (known as target in this invention) to be taken on a container 4111 and follows the instructions to initiate pill identification activity 4114. In accordance with the invention, as illustrated in FIG. 4, the patient follows the instruction to end the pill identification activity 4114 to perform preparation activities 4120 for the next instruction guided activity 4121.

In some embodiments, the instructions for pill identification activity 4114 may include patient placing the target on the container with mobile device camera aimed at the target such that patient can adjust distance of the mobile device camera, to focus and view the target within the view port displayed on the mobile device's display.

In some embodiments, the instructions for pill identification activity 4114 may include turning on or off additional light in the space where activity is performed, or increasing or decreasing luminance of the background light. In some embodiments, the mobile device may automatically sense the ambient light intensity to turn on and control mobile device embedded flash light directed on the target, or may request the patient to do so.

In some embodiments, pill identification activity may be completely omitted, where upon the patient is instructed to perform a self-report activity to input medication event data that includes, but not limited to the type and number medications, the time and location of medication. In accordance with this invention, self-report activity is a system-instructed human activity 4121 and self-reported medication event is a medication event outcome measure 4181.

In accordance with the invention, as illustrated in FIG. 4, the medication event outcome measures 4181 are communicated by the component 4182 to the back-end processing system as medication event data 2110 (illustrated in FIG. 2)

and stored in non-transitory computer readable storage medium as the recent event data in a medication event history data system 4185.

Figure 5:
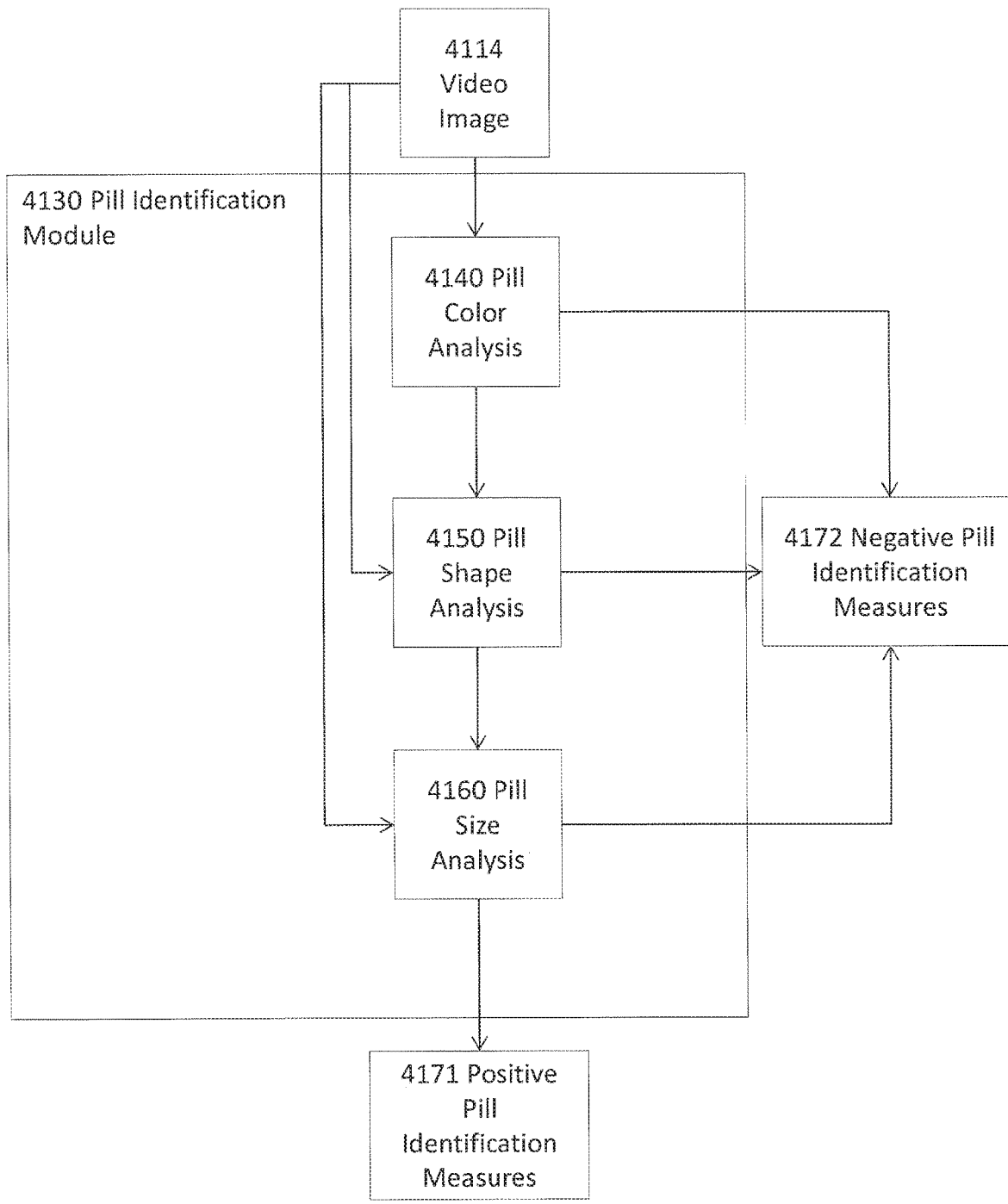
FIG. 5 depicts the flow chart of pill identification module of the medication event logging process in accordance with an embodiment of the present invention

In some embodiments, in accordance with the invention, FIG. 5 describes the details of the pill identification component 4130. In some embodiments, a pill is a medicinal substance in a various shapes and mass meant to be swallowed directly with or without any external fluid, swallowed sublingually with or without any external fluid, or chewed and then swallowed with or without any external fluid. FIG. 5 describes the 3 analysis components included in the pill identification component in accordance with the invention. In accordance with the invention, FIG. 5 illustrates that the color analysis component 4140 is applied to the video images, which either outputs a region with expected pill color, or outputs negative pill identification measures 4172.

Figure 6:
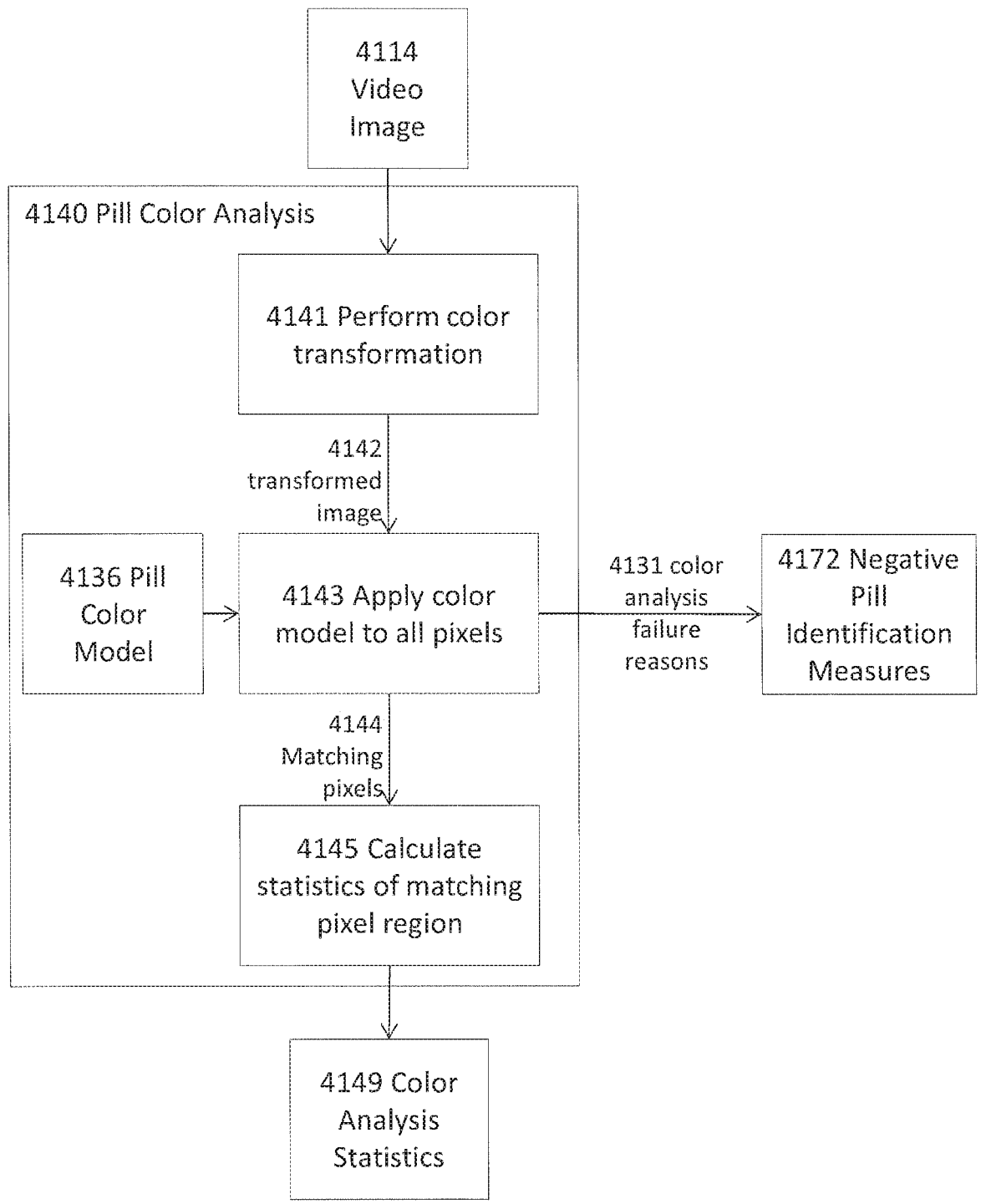
FIG. 6 depicts the flow chart of pill color analysis component of the pill identification module in accordance with an embodiment of the present invention.

In accordance with the invention, FIG. 5 illustrates that the video images and output from pill color analysis component 4140 is analyzed by pill shape analysis component 4150, which either outputs a region with expected pill shape, or outputs negative pill identification measures 4172. In accordance with the invention, FIG. 5 illustrates that the video images and output from pill shape analysis component 4150 is analyzed by pill size analysis component 4160, which either outputs positive pill identification outcome measures 4171, or outputs negative pill identification measures 4172. In accordance with the invention, FIG. 6 describes the detail steps of pill color analysis component 4140. FIG. 6 describes the first step, which includes color transformation 4141 to generate a transformed image 4142. In some embodiments, transformation may include, but not limited to histogram equalization, normalization, adaptive normalization, grey word normalization, comprehensive color normalization. FIG. 6 describes the second step which includes application pill color model 4143 to find color model-matching pixels in the images. In some embodiments, color matching algorithms may include, but not limited to histogram matching, probability distribution matching and other statistical matching techniques. FIG. 6 describes the output of step 4143 is either a region of matching pixels 4144, or negative pill identification measures 4172. As described in FIG. 6, the color analysis reason 4131 includes, but not limited to not having number and percentage of matching pixels greater or smaller than set thresholds defined within pill color analysis component. FIG. 6 describes the third step of calculating statistics from the matching pixels 4145 and generating color analysis statistics 4149, which in some embodiments may include, but limited to area percentage, average position, number of pixels, etc.

Figure 7:
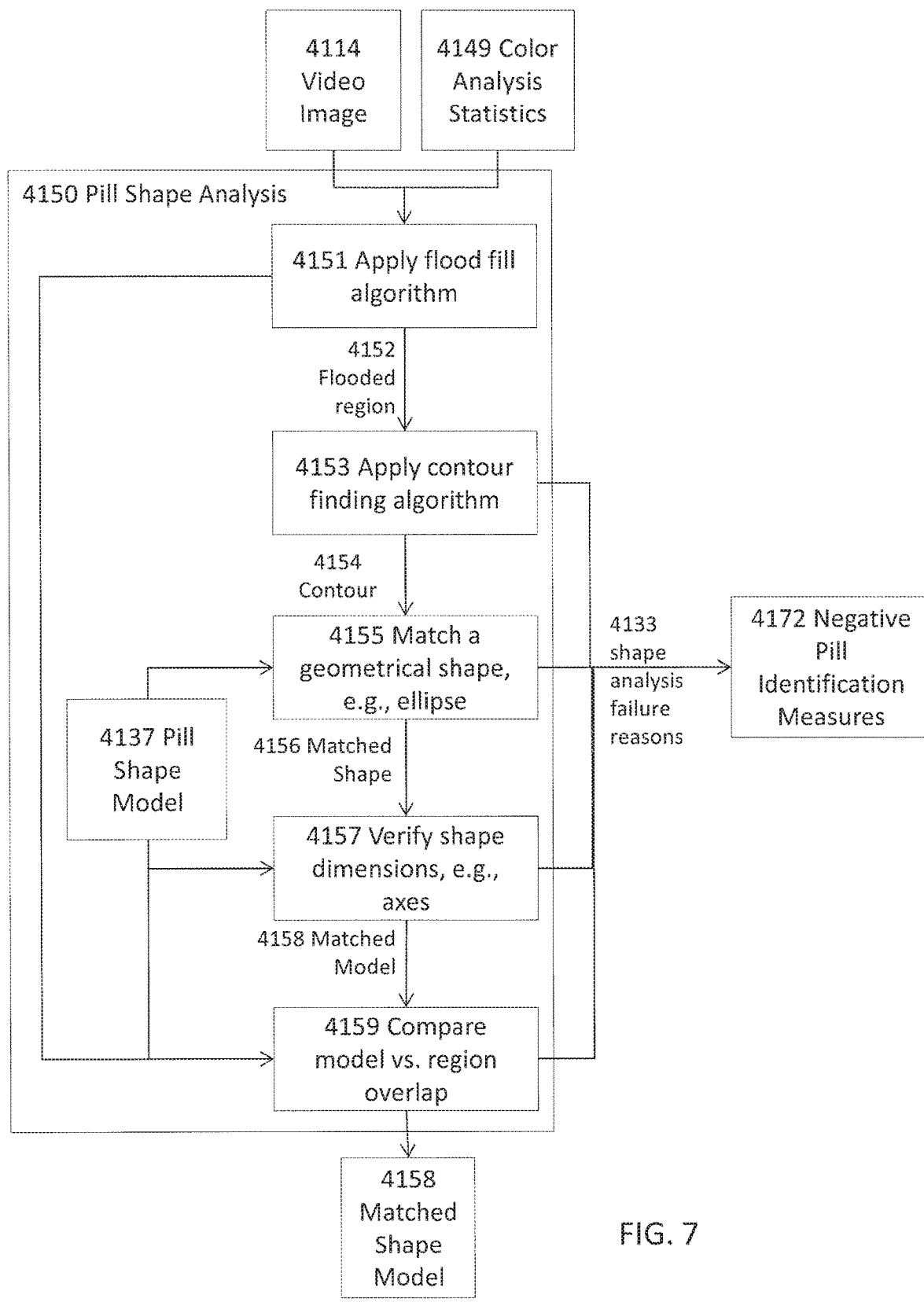
FIG. 7 depicts the flow chart of pill shape analysis component of the pill identification module in accordance with an embodiment of the present invention.

In accordance with the invention, FIG. 7 describes the detail steps of pill shape analysis component 4150. FIG. 7 describes the first step of applying flood fill algorithms 4151 on the video images 4115 using color analysis statistics 4149. FIG. 7 describes the second step of applying contour finding algorithm 4153 around the flooded region 4152. FIG. 7 describes the third step 4155 of matching geometrical shapes from the pill shape model 4137 to the contour 4154 to determine best matched shape 4156. FIG. 7 describes the fourth step 4157 of computing the shape dimensions and comparing them against the pill shape model 4137 to compute matched model of the shape 4158. FIG. 7 describes the fifth step 4159 of comparing pixel area overlapping the matched shape model 4157 and the flooded region 4152 to determine eligibility of the shape model 4157. FIG. 7 describes that the steps 4153, 4153, 4155, 4157 and 4159 also results in negative pill identification measures 4172 with shape analysis failure reasons. In some embodiments, the shape analysis failure reasons 4133 may include, but not limited to inability of determining a contour, inability of fitting shape, inability of determining a matching shape model, or rejecting the model for not meeting threshold overlapping criteria.

Figure 4A:
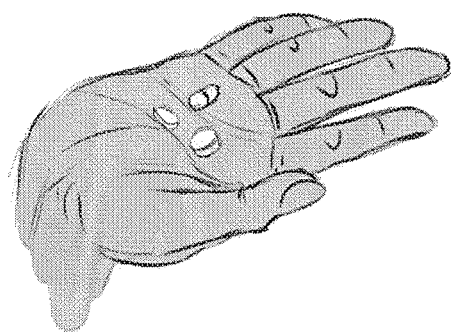
FIG. 4a illustrates the containers used to present medications to the mobile device optical sensors during medication event logging process in accordance with an embodiment of the present invention.
Figure 4A:
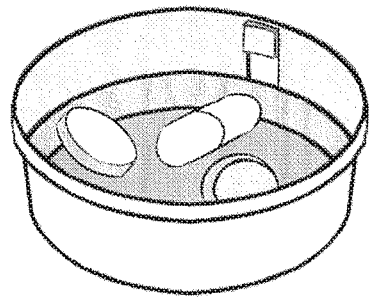
Figure 8:
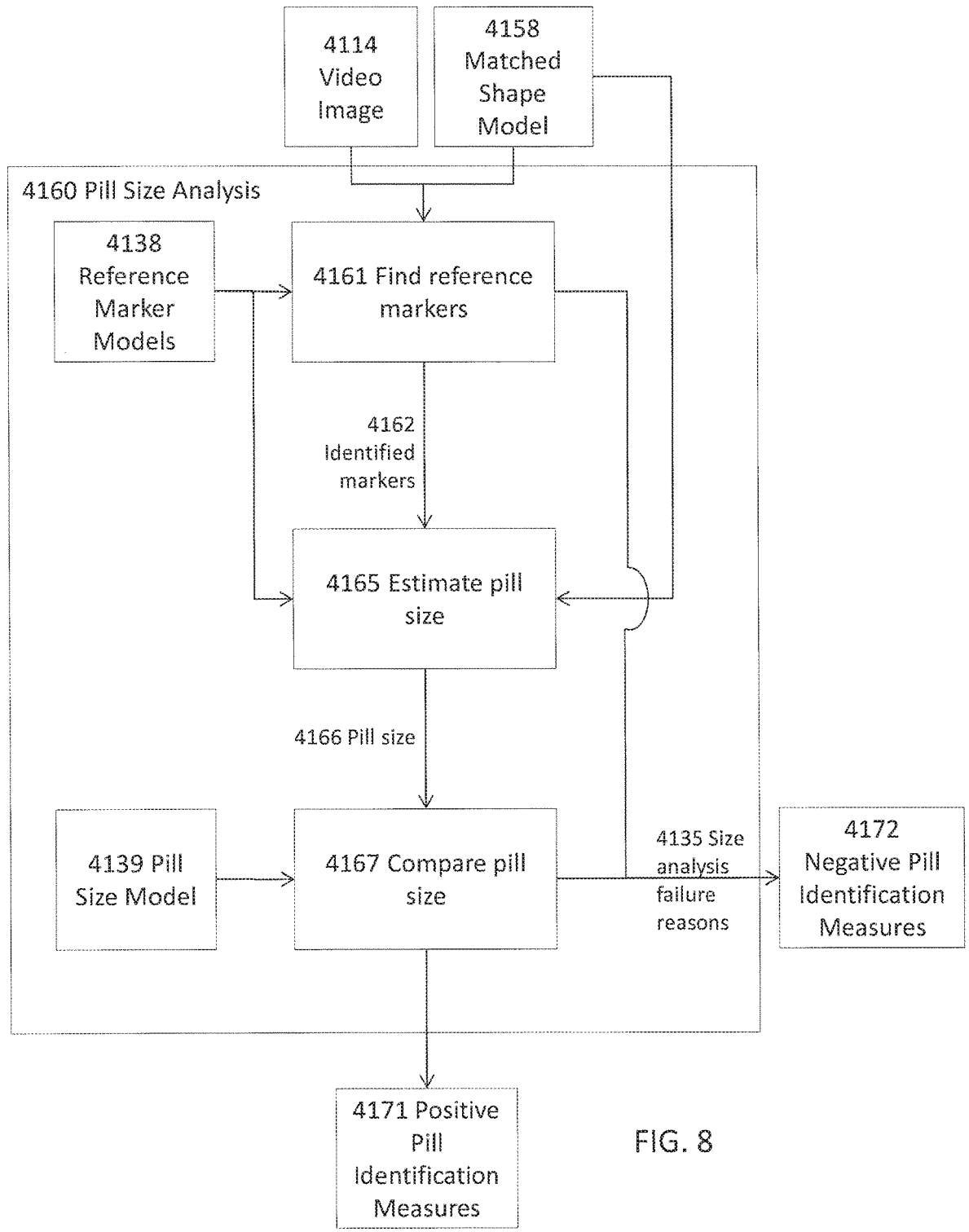
FIG. 8 depicts the flow chart of pill size analysis component of the pill identification module in accordance with an embodiment of the present invention.

In accordance with the invention, FIG. 8 describes the detail steps of pill size analysis component 4160. In accordance with the invention, reference marker model 4138 is associated with containers used by the patient to place the pills and show them to the mobile device camera. In some embodiments, the containers may include palm of the hand 4112 in FIG. 4a, which is the most popular method of taking medications. In accordance with the invention, the biomarker features such as palm lines whose dimensions of the features (such as length, thickness, or orientation of the palm lines) are the reference marker model 4138 when palm is used as a container to take medication. In some embodiments, the containers may include inside of the pill box cap 4113 in FIG. 4a, which is another popular method of taking medications. In accordance with the invention, the dimensions such as diameter and circumference of the cap are the reference marker model 4138 when pill box cap is used as a container to take medication. In some embodiments, the container may include specialized cups or trays with optically visible markers to serve as known or calibrated reference marker model 4138 for the component 4160. In accordance with the invention, the reference marker model is known to the component 4160 by virtue of the container that the patient is instructed to use to place the pills while taking medication. FIG. 8 describes the first step 4161 of identifying reference markers using reference marker model 4138 known to the component 4160. In some embodiments, the step 4161 may use other mobile device sensor data such as gyroscope and proximity sensors to adjust for shaking of the device and possibly hand holding the pill. FIG. 8 describes the second step 4165 of estimating pill size 4166 using identified markers 4162, reference marker model 4138, and matched pill shape model 4158. FIG. 8 describes the third step 4167 of comparing pill sizes with the pill size model 4139 that either produces the positive pill identification outcome measures 4171, or negative pill identification outcome measures 4172. FIG. 8 describes that the steps 4161 and 4167 also result negative pill identification outcome measures with size analysis failure reasons 4135. In some embodiments, the size failure reasons may include inability to identify reference markers or rejection of pill size due to the mismatch between the model and derived pill size.

Figure 9:
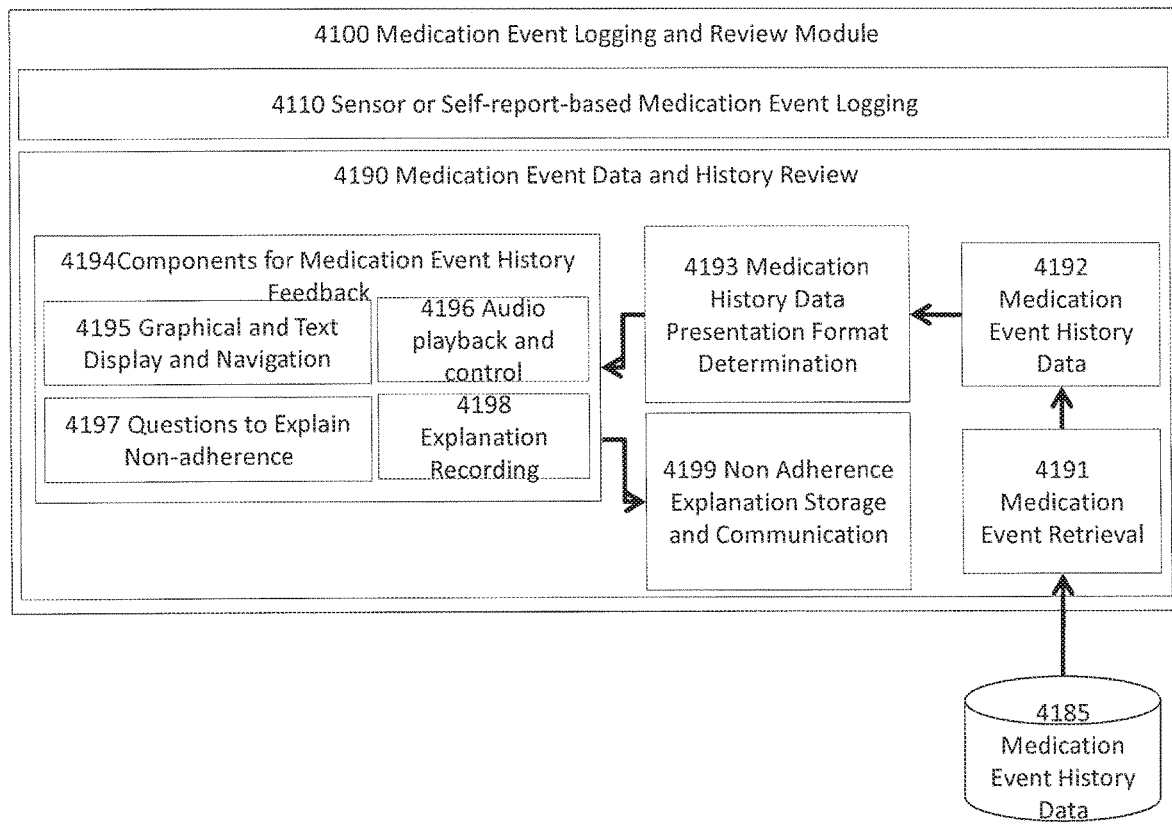
FIG. 9 describes the details of medication event data and history review in accordance with an embodiment of the present invention.

FIG. 9 illustrates the details of medication event data and history review component 4190 of the module 4100. In accordance with the invention as illustrated in FIG. 9, the medication event history data are retrieved and presented to the patient for review and feedback. In some embodiments, the event history data may be presented as an intervention message from the back-end processing system. In some embodiments, the patient directly accesses and reviews event history data and provides feedback and explanation. FIG. 9 illustrates component 4191 retrieving event history data 4192 and component 4193 determining the presentation format for the history data. In some embodiments, the presentation and feedback includes, but not limited to graphical and text display of the data along with audio playback, and questions to explain the non-adherence patterns. In some embodiments, the non-adherence patterns may be highlighted, enumerated, or spoken to draw attention to the patterns. In some embodiments, explanations may be provided by the patient as a narrative description, selecting from multiple choices (pre-defined set of descriptions), or verbal dictation. In accordance with the invention, the explanations provided by patient are identified as non-adherence explanation data 2160 and is defined as part of the patient data 2100. FIG. 9 illustrates component 4199 stores and communicates the explanation data to the back-end processing system. In some embodiments, the explanations may result in providing intervention messages consisting of tips and advices of overcoming the barriers explained by the patient. In accordance with this invention, the component 4300 (FIG. 2) allows patient to log their medication experience and review historical record of the experiences. In accordance with this invention, a medication experience may include, but not limited to the feedback on medication schedules, current and new personal barriers to taking medication, side effects they are experiencing, the side-effect coping strategy or remedial actions they are following, and effectiveness of the side effect coping strategies they have been following. In accordance with the invention, the component 4300 provides the feedback format to prompt and collect patient's medication experience data. In some embodiments, the patient may be provided with an intervention message to present an observation and collect patient's medication experience. For example, a patient who has consistently reported side-effect as possible reason for non-adherence will be prompted with intervention message to elaborate on their side effect experiences. In some embodiments, the patient may be presented with the list of possible medication side effects along with likelihood of those side effects as reported from the clinical studies and explanation of the symptoms, symptom onset period, and the reasons for experiencing the systems so that patient maintains a diary of the side effects via the component 4300. In some embodiments, the component 4300 presents the patient with a list of coping strategies for the side effects they experience, and allows to patient to also keep track of the coping strategies they apply, when they apply, what effects they experience after applying the coping strategies. In accordance with the invention, the data 2171 (FIG. 10) on medication side effect experiences and the data 2172 (FIG. 10) on application of coping strategy and subsequent effect on the side effect symptoms are part of medication experience data 2170, which is stored and communicated the back-end processing system by the component 4300. For example, a patient logging nausea as side effect, will be presented with coping strategies such as taking medication after or during the meal, taking at least 8 ounces of water with medication, eating easily digestible food with medication, etc.

Figure 10:
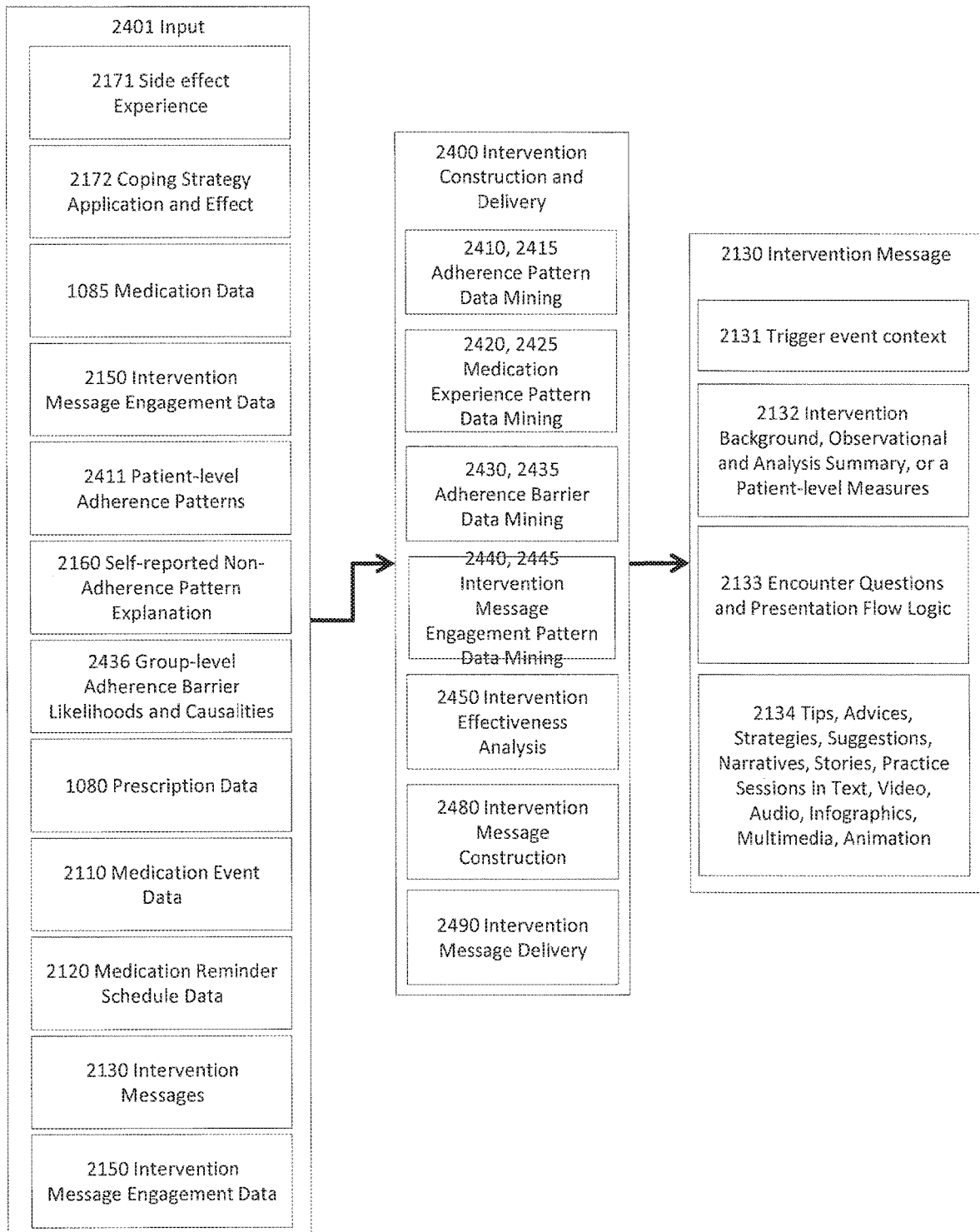
FIG. 10 describes the details of input and outs of intervention construction and delivery module of back-end processing system in accordance with an embodiment of the present invention.

In some embodiments in accordance with the invention described in FIG. 10, intervention message construction and delivery module 2400 automatically constructs intervention messages 2130 and delivers them to the user-end apparatus or system. In accordance with the invention, the module 2400 takes various types of input 2401 and applies various types of data mining, statistical analysis, model building, optimization, and message composition and delivery trigger contextualization algorithms to determine and deliver intervention messages 2130 to each patient. The input to the intervention message construction and delivery 2400 described in FIG. 10 includes but not limited to patient data on side effect experiences 2171, the coping strategy applied and its effect 2172, medication label data 1085 (medication warning, adverse event reports obtained from third party external sources), all patient's intervention message engagement data 2150, each patient's prescription data 1080, each patient's medication event data 2110, each patient's medication reminder schedule data 2120, patient-level adherence patterns 2411 of all patients, patient's self-reported explanation of non-adherence patterns 2160, group-level adherence barrier likelihood 2436 (consisting of parameters set by the service provider and updated by the intervention construction and delivery module 2400), intervention messages delivered to each patient 2130, each patient's intervention message engagement data.

In accordance with the invention described in FIG. 10, the intervention message construction and delivery module 2400 consists of, but not limited to components—adherence pattern data mining 2410 and 2415, medication experience pattern data mining 2420 and 2425, adherence barrier data mining 2430 and 2435, intervention message engagement pattern data mining 2440 and 2445, and intervention effectiveness analysis 2450. The data mining and analysis components produce various types of likelihood, patterns, correlation, trends and causal links as described in FIG. 10, which are processed by intervention message construction module 2480 to produce a set of intervention messages 2130 targeted for each patient that are delivered in accordance to the delivery schedule and context determined by intervention message delivery module 2490. In accordance with the invention described in FIG. 10, an intervention message 2130 consists of types of information, but not limited to trigger event context 2131, the background description, observational and analysis summary, or patient-level measures 2132 presented to a patient as intervention context, a set of questions with a presentation flow logic 2133 to find new information from the patient or revise previous information provided by the patient, and educational contents 2134 that are presented at the end or in between the questions prompted to the users. The educational content 2134 includes, but not limited to tips, advices, strategies suggestions, narratives and stories, and practice sessions designed with goal for the patients to learn techniques to overcome barriers and side effect coping strategies. The education content 2134 are presented in the format, but not limited to text, video, audio, multimedia, graphical, pictorial, and animation with audio and captions. The examples of intervention trigger event context 2131 includes, but not limited to date and time, geographical location of the mobile device and other mobile device sensor data accessible to the user-end apparatus and system 4000.

Figure 11:
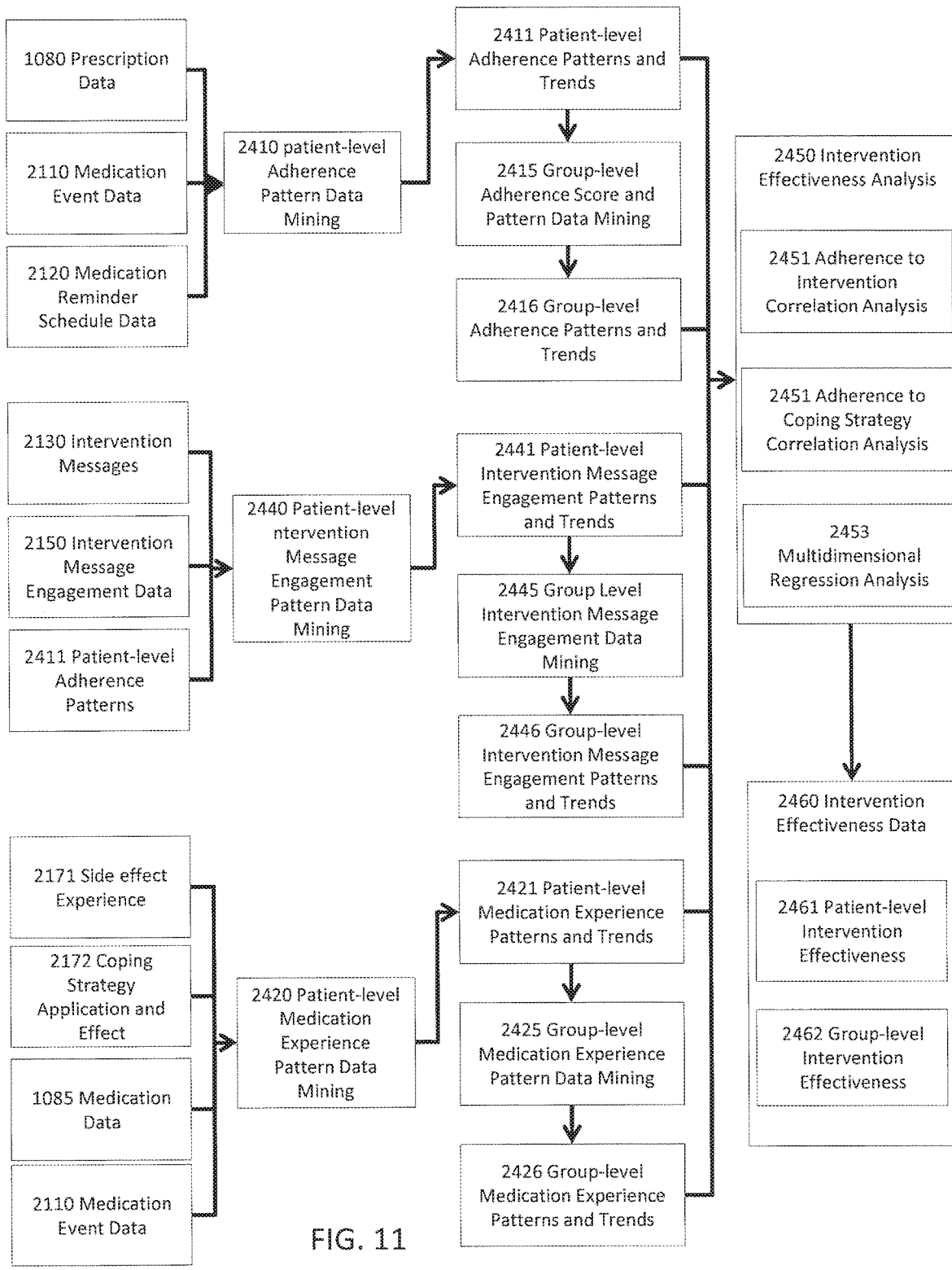
FIG. 11 describes the details of different data mining components of intervention construction and delivery module of back-end processing system in accordance with an embodiment of the present invention.

FIG. 11 describes the details of patient-level adherence pattern data mining 2410, patient-level medication experience pattern data mining 2420, patient-level intervention message engagement pattern data mining 2440, and intervention effectiveness analysis 2450. All patient-level data mining components 2410, 2440, and 2420 determine patient-level patterns and trends such as patient-level adherence (or non-adherence) patterns and trends 2411, patient-level intervention message engagement patterns and trends 2441, and patient-level medication experience patterns and trends. In accordance with the invention described in FIG. 11, the patient-level patterns and trends for all patients are mined by group-level data mining components such as group-level adherence score and pattern data mining 2415, group-level intervention message engagement data mining 2445, and group-level medication experience pattern data mining 2425 to determine group level patterns and trends such as 2416, 2446, and 2426. The patient-level and group-level patterns and trends are analyzed by intervention effectiveness analysis module 2450 to determine the patient-level and group-level intervention effectiveness data and store them in a non-transitory computer storage medium. The module 2450 includes correlation and regression analysis, and other statistical analysis algorithms not described in FIG. 11. In accordance with the invention, intervention effectiveness is one or more numerical or categorical values or combination thereof indicating the effect of pre-defined message contents on the change in one or more patient adherence scores and patterns. The examples of intervention effectiveness is a multidimensional data that includes, but not limited to correlation between various types of intervention messages to the adherence improvement over time with respect to adherence barriers, the efficiency in terms of pace of adherence improvement, lead time to practicing intervention, and intervention learning, preference, practicality, habit-formation and usability indices and their change with time since they are practiced.

In accordance with the invention as described in FIG. 11, the prescription data 1080, medication event data 2110, and patient's medication reminder schedule data 2120 is processed by patient-level adherence pattern data mining algorithms 2410 to produce patient-level adherence patterns and trends 2411 and store them in a non-transitory computer storage medium. In accordance with the invention, adherence scores and patterns are numerical or categorical or combination thereof characterization of one or more patient's adherences to taking medication. Examples of adherence patterns include, but not limited to missing and overdose patterns such as missing every alternate day, missing second dose every day, or overdosing while being at home. Medication event data 2110 includes all contextual data such as geographical and patient's vital health statistic as collected by mobile device sensors. The adherence pattern trend data includes change of patterns over several days of taking medication. The patient-level adherence patterns and trends 2411 is further mined at various group levels defined by the service provider, using group level data mining algorithms 2415 that includes, but not limited to classification, clustering, principal component analysis, to produce group level adherence patterns and trends 2416. In accordance with the invention as described in FIG. 11, the intervention messages 2130 that have been presented to a patient, patient's intervention message engagement data 2150, and patient-level adherence patterns (determined from 2410 data mining components) are processed by patient-level intervention message engagement pattern data mining 2440 to produce patient-level engagement patterns and trends and store them in a non-transitory computer storage medium. In accordance with the invention, the intervention message engagement data includes, but not limited to the answers to the intervention message questions 2133 prompted to the patients, the duration of answering the questions, the time, location and other mobile device sensor data at the time of answering questions, the number of time questions are read, the number of times answers are reviewed, the number of times intervention message contents 2134 are read, the duration for which the intervention message contents are read, and the statistics on the trigger event context 231 when intervention message contents are reviewed, the number of times and duration for which a tip, suggestion, advice, focal points in the stories 2134 is put into practice by the patient, the lead time between when a tip, suggestion, advice, and stories 2134 presented to the patient before he or she puts the 2134 into practice. In accordance with the invention, engagement scores and patterns are numerical or categorical or combination thereof characterization of one or more patient's engagement with intervention messages. Example of engagement patterns include interventions questions that show large change in answer scale or score in one week, the interventions with night time engagement has higher probability of more than 3 minutes of engagement, etc. The patient-level engagement patterns and trends 2441 is further mined at various group levels defined by the service provider, using group level data mining algorithms 2445 that includes, but not limited to classification, clustering, principal component analysis, to produce group level engagement patterns and trends 2446. In accordance with the invention as described in FIG. 11, the side effects 2171 experienced by the patient, the coping strategy applied by the patient and patients assessment of its effect of the strategy on managing ensued side effects 2172, the medication label data 1085 published by prescription drug manufacturers 1085, and patient's medication event data 2110 are processed by patient-level medication experience pattern data mining 2420 to produce patient-level medication experience patterns and trends 2421 and store them in a non-transitory computer storage medium. The examples of side effects include, but not limited to nausea, insomnia, headache, vivid dreams, abdominal pain, gas, flatulence, dry mouth, vomiting, weight gain, anxiety etc. The examples of coping strategy include, but not limited to drinking water, avoiding caffeine drinks, doing meditation, moderate physical activity, etc. The effect of copy strategy may include, but not limited to the time when a coping strategy was first and last applied, and the severity of side effect before coping strategy was applied and the latest severity. In accordance with the invention, medication experience scores and patterns are numerical or categorical or combination thereof characterization of one or more patient's experience from taking medication. Examples of patient-level medication experience pattern include two miles of walking three days of every week reduces the level anxiety by half. The patient-level medication experience patterns and trends 2421 is further mined at various group levels defined by the service provider, using group level data mining algorithms 2425 that includes, but not limited to classification, clustering, principal component analysis, to produce group level engagement patterns and trends 2426.

Figure 12:
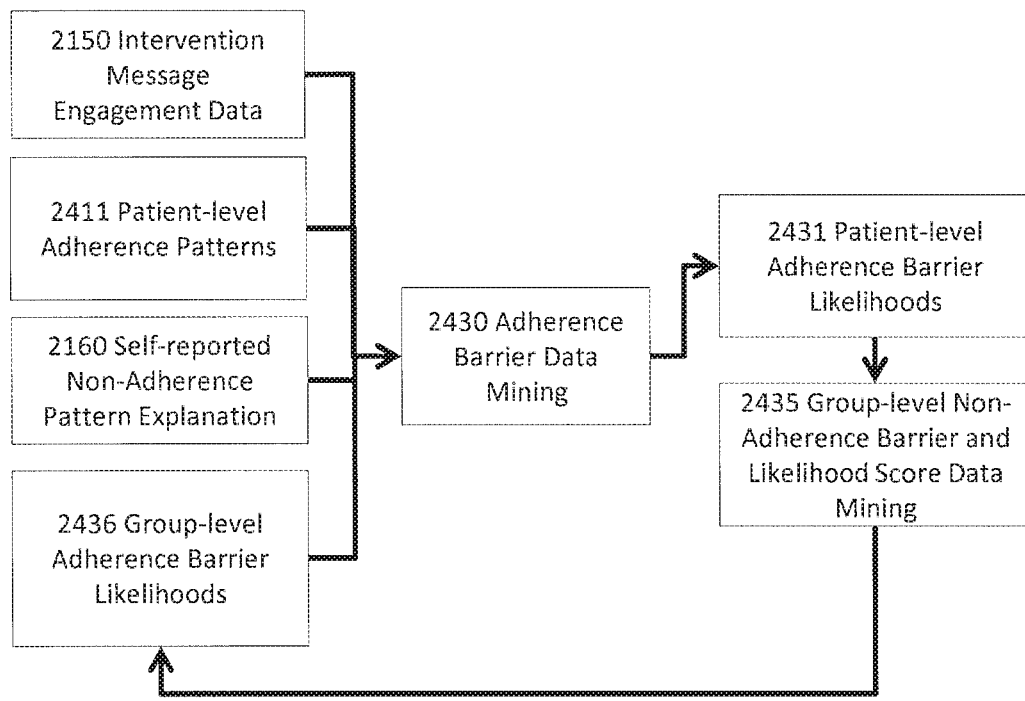
FIG. 12 describes the details of adherence barrier data mining components of intervention construction and delivery module of back-end processing system in accordance with an embodiment of the present invention.

In accordance with the invention as described in FIG. 12, the patient's intervention message engagement data 2150, patient-level adherence patterns 2411, patient's self-reported adherence (or non-adherence) pattern explanation 2160, and group-level adherence barrier likelihood 2436 are processed by adherence barrier data mining module 2430 to determine patient-level adherence barrier likelihood 2431. In accordance with the invention, a patient self-reports explanation for their non-adherence aspartof medication event review 4100 and intervention engagement 4200. The self-reported explanation consists of the adherence barriers that patient admits to be likely factors for his or her non-adherence. The group-level barrier likelihood 2436 consists of initial parameters set by the service provider for each group that are updated by the group-level non-adherence barrier likelihood data mining 2435 by mining over all patient's patient-level adherence barrier likelihood 2431. In accordance with the invention, adherence barrier likelihood is one or more numeric values indicating the likely reasons for one or more patient not taking medication. An example of barrier likelihood includes probability that a barrier will make a patient or group of patients to show a non-adherence pattern in one, two or three weeks since the start of medication.

Figure 13:
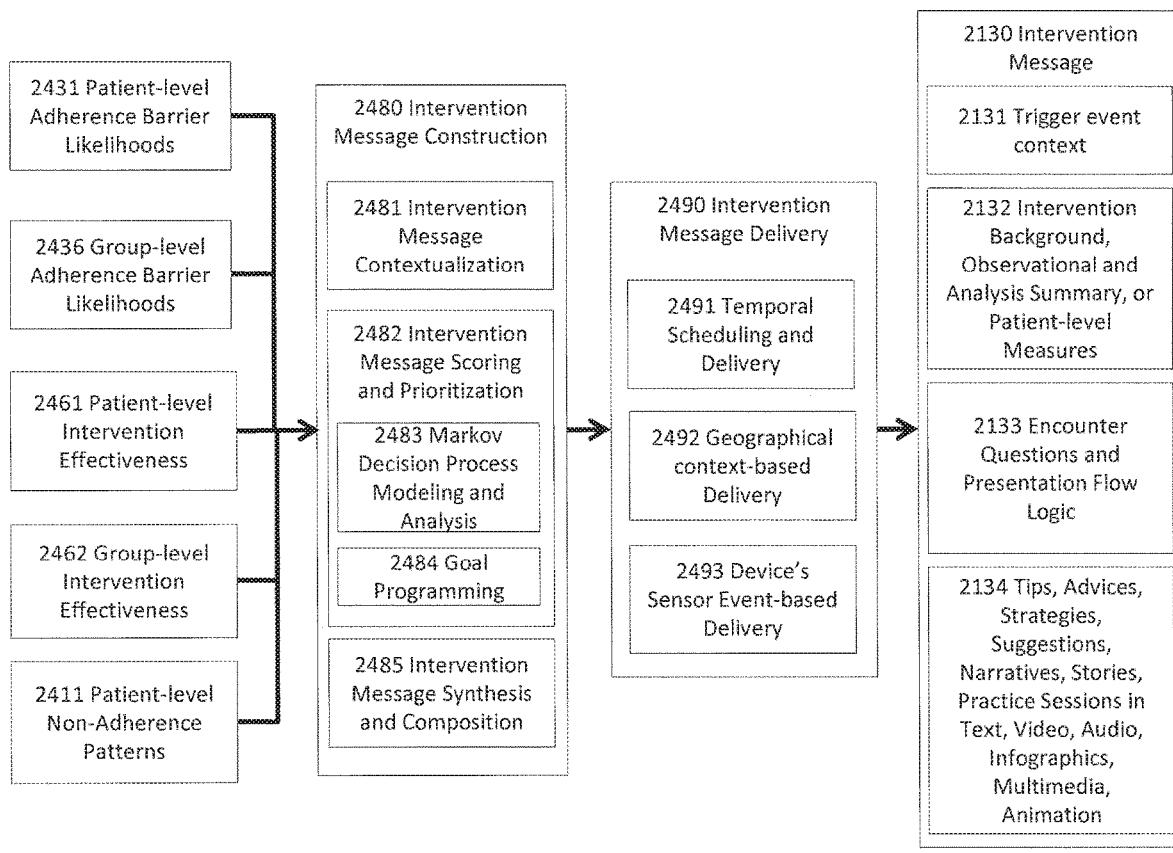
FIG. 13 describes the details of intervention construction and delivery module of back-end processing system in accordance with an embodiment of the present invention.

In accordance with the invention as described in FIG. 13, the calculated patient and group-level barrier likelihoods 2431 and 2436, patient and group-level intervention effectiveness data 2461 and 2462, and patient-level non-adherence patterns 2411 are processed by intervention message construction module 2480 to construct an intervention message with 2132, 2133, and 2134 data. As described in FIG.

13 the message contextualization component 2481 formulates the background, observational and analysis report, and adherence and engagement measures that are needed to be reported to the patient, which makes up 2132 data of the intervention messages. The scoring and prioritization component 2482 prioritize the intervention that are critical for the patient to view and address, which uses techniques that include, but not limited to Markov decision process modeling and analysis 2483, dynamic or goal programming 2484. The synthesis and composition component 2485 formulate the intervention questions and the presentation flow logic 2133, and contents providing tips, advices, and suggestions 2134. The prioritized intervention messages are delivered to the user-end apparatus or system at specific contexts determined by the message delivery module 2490. Some messages are simply scheduled on a time line as scheduled and delivered by component 2491; some messages are delivered by component 2492 when the user-end apparatus is determined within a geographical area; some messages are delivered when the mobile device sensor data from the user-end apparatus reaches a set value determined by the component 2493. The delivery conditions in accordance to this invention are not limited to embodiments described here. In some embodiments in this invention, the back-end processing system 2000 provides the key functionality of the automated adherence improvement system by constructing personalized interventions to the patients with a targeted goal to improve their adherence behavior.

In some embodiments, the back-end processing system 2000 also provides key tools for Medication Therapy Management (MTM) program to set up patient information and monitor patient and group-level adherence metrics and key tools for MTM service providers to intervene patients at the patient and group-level. The metrics calculator 2300 module of the back-end processing calculates patient-level and group-level adherence behavior statistics from both patient data 2100 and adherence and intervention patterns, likelihoods, trends and correlations determined by module 2400. In some embodiments, the adherence behavior statistics may include, but not limited to counts, average, maximum and minimum values, standard deviation, confidence intervals, and various statistical measures of coefficients and indices. In some embodiments, the 2300 module allows external systems authorized to connect to the back-end processing system via communication medium 1020 (e.g., hypertext transfer protocols, database connections, or any other Internet communication protocol) to access and obtain patient and group-level metrics. In some embodiments, the 2300 module allows authorized external systems to obtain both raw patient data and module 2300 and 2400 derived or analyzed data, together known data 2720 in this invention as described in FIG. 14.

In accordance with the invention, the notification and messaging 2500 module of the back-end processing provides templates to construct and set up customizable intervention messages and notifications. In some embodiments, the module 2500 allows external systems authorized to connect to the back-end processing system via communication medium 1020 to access and obtain intervention message templates, define intervention messages with custom trigger event context, custom questions and question presentation flow, and custom contents, and set up target patients or groups of patients to who the custom messages are delivered including specifying the mode of delivery such as emails, text messages, automated voice recording, or in-app messages. In some embodiments, the module 2500 also allows authorized external systems to schedule or send immediately short notifications via mobile device's notification systems. In accordance with this invention, such customized communication data that includes intervention messages and notifications are identified as custom patient communication data 2710 as described in FIG. 14.

In accordance with this invention, the system authorization and patient enrollment 2600 module is a key functionality of the back-end processing system that allows external medication adherence service providers to connect and communicate with the system. In some embodiments, the module includes setting all access authorization for the back-end processing system to obtain 2710 and 2720 data. In some embodiments, 2600 module allows medication service providers via their service provider-end apparatus or system 3100 to enroll patients and authorize the back-end processing system to maintain patient data 2100 and improve the patient's adherence measures through automated intervention. In some embodiments, the medication adherence service provider via their service provider-end apparatus or system 3100 authorize the back-end processing system to pull medication label data 2750 (e.g., medication guide, indications and contraindications, warnings, structure product list (SPL), drug interactions, reported adverse effects, common remedial actions) from authorized medication label data storage, maintenance and retrieval systems 3300 (e.g., Food and Drug Administration, Pharmaceuticals, Pharmacies, and other such organizations), and pull patient-specific prescription data 2740 from authorized prescription data storage, maintenance and retrieval systems (e.g., E-Prescription service providers, prescriber's Electronic Health Record (EHR) systems, Pharmacies, etc.). In some embodiments, the adherence service provider may directly enter patient prescription data while enrolling a patient or adding and updating prescription data for enrolled patient. In some embodiments, using 2600 module, the adherence service provider may also perform various system level set up that includes, but not limited to defining groups, intervention messages, measures, thresholds, and intervention construction and delivery parameters, data mining and statistical parameters, setting up algorithms for data mining and statistical analysis. In some embodiments, in accordance with this invention as described in FIG. 14, the system set up data including system authorization and patient enrollment data is indicated as 2730 system set up data.

Figure 15:
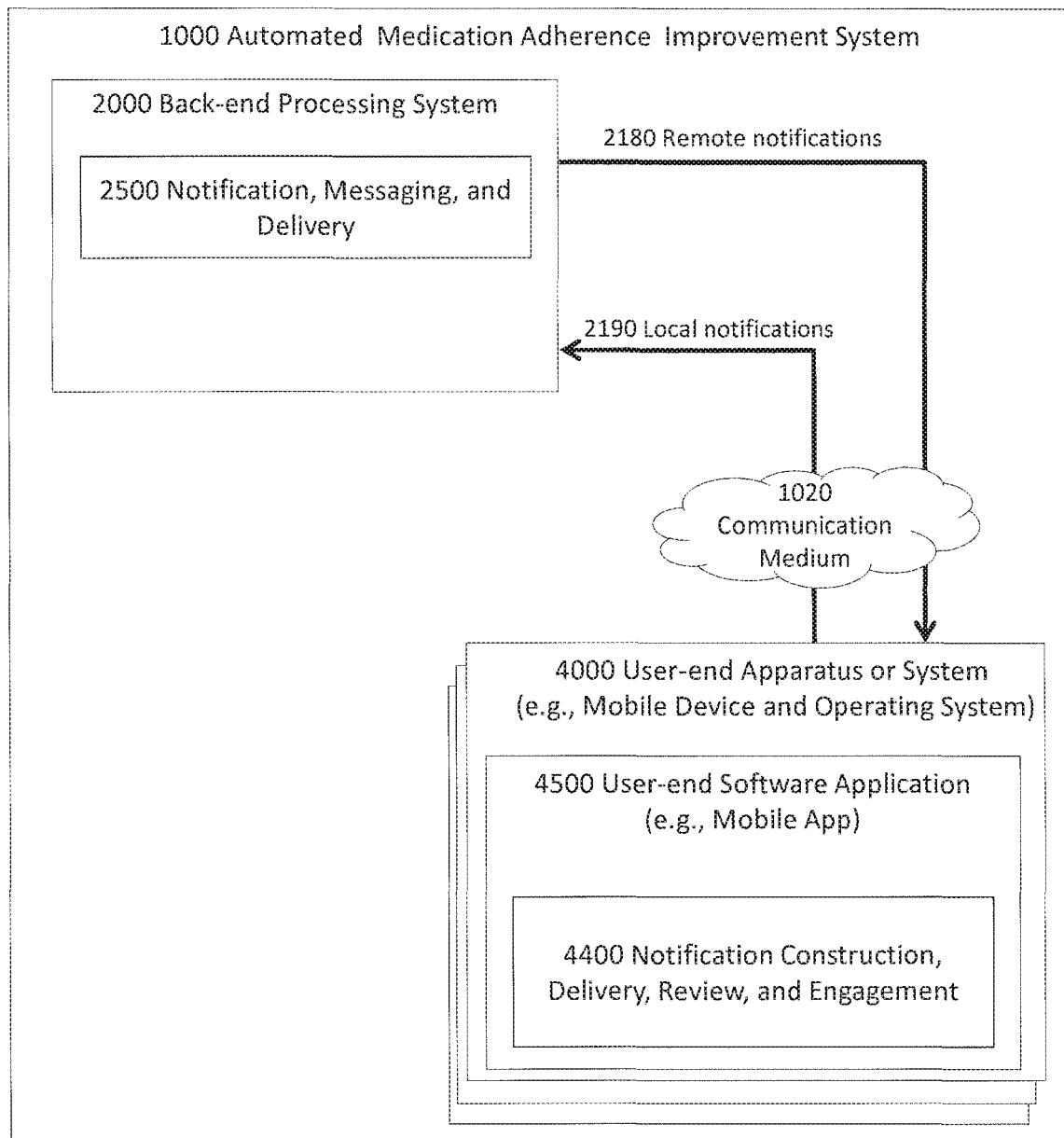
FIG. 15 describes the details of the notification and messaging component coupling between back-end and user-end systems in accordance with an embodiment of the present invention.

In accordance with this invention as illustrated in FIG. 15, the component 2500 of the back-end processing system and component 4400 of the user-end apparatus or system are coupled together communicatively and are critical components for notification construction, delivery, review and engagement. In accordance with the invention, a patient's engagement in using component 4200, 4100 and 4300 is reduced without the component 2500 and 4400. In accordance with the invention as illustrated in FIG. 10, three types of notifications are supported—remote notifications 2180 from the back-end systems generated by the 2500 component, and local notifications generated by the component 4400. In some embodiments, the remote notification 2180 may include mobile device operating system level notifications that are displayed and controlled by the device's operating system that are often called as push notifications. In some embodiments, a push notification may consist of a short text that patient has new intervention messages. In some embodiments, a push notification may consist of a short text that patient has a new or update to his or her prescription. In some embodiments, the remote notification 2180 may include messages that are intended for viewing using third-party applications on the mobile devices such as electronic mails (emails) and instant messaging, short text messaging, and social media applications. In some embodiments, the remote notification 2180 may include voucher and discount messages that can be opened or viewed using third-party applications on the mobile devices such as gaming and other healthcare applications. In accordance with the invention, a local notification is either an event-based reminder notifications, alerting symbols with data that may appear on the user-end apparatus or system 4000 that can only be opened or viewed for details using the user-end software application 4500, or alerting symbols with data that appear from within the user-end software application 4500. In some embodiments, the event in an event-based reminder notification may consist of time instance, location, or other mobile device sensor data available to the software application 4500. In some embodiments, a reminder notification may be issued for taking medication at an event. In some embodiments, a reminder notification may be issued for applying coping strategy at an event. In some embodiments, an alerting symbol may consist of an alert that patient has not engaged in certain number of intervention messages, or patient may log a medication event, or schedule a medication reminder because of a new prescription obtained from the back-end system.

While the invention has been taught with specific reference to these embodiments, one skilled in the art will recognize that changes can be made in form and detail without departing from the spirit and scope of the invention.

The invention claimed is:

1. A medication event logging method, comprising the steps of:
   (1) recording video activity of patient showing at least one pill on the palm of a patient's hand, or on a pill bottle cap with optically visible reference marks to optical sensors on a mobile computing device;
providing, on a display of the mobile computing device, instructions to capture the video activity;
   (2) storing the recording of the video activity to a non-transitory computer readable storage medium on the mobile computing device;
   (3) employing a processor of the mobile computing device to process video sequences to compare with predefined or iteratively adjusted parameters and measure a medication event outcome including:
      (a) analyzing pill color including steps of:
         i. performing a color transformation of a respective image of a video sequence to provide a transformed image;
         ii. applying a pill color model to the transformed image;
         iii. calculating color match statistics; and
      (b) analyzing pill shape, including steps of:
         i. applying flood fill algorithms to the respective image based on the color match statistics;
         ii. applying a contour matching algorithm to a flooded region of the respective image;
         iii. matching geometrical shapes from a pill shape model to a respective contour to determine a best match shape;
         iv. computing shape dimensions of the best matched shape;
         v. comparing the shape dimensions to the pill shape model to provide a matched shape model; and
         vi. compare a pixel area overlapping the matched shape model and the flooded region to determine eligibility of the shape;
      (c) analyzing pill size, including:
         i. identifying reference markers in the respective image;
         ii. estimating pill size based on the reference markers, a reference marker model and the matched shape model;
         iii. comparing estimated pill size with a pill size model;
      (d) determining a pill identification outcome based on the analyzing of the pill color, pill shape and pill size;
   (4) recording a second video activity showing the at least one pill in the mouth of the patient and the patient opening the mouth, the patient swallowing the at least one pill and then showing the mouth empty of the at least one pill to the optical sensors on the mobile computing device;
   (5) providing, on a display of the mobile computing device, instructions to capture the second video activity;
   (6) storing the recorded second video activity related to the patent's mouth to the non-transitory computer readable storage medium on the mobile computing device;
   (7) determining, by the processor of the mobile computing device, a second medication event outcome based in the second video activity and predefined or iteratively adjusted parameters; and
   (8) storing the second medication event outcome to the non-transitory computer readable storage medium on the mobile computing device,
wherein the medication event outcome is based on both the pill identification outcome and the second medication event outcome;
   (9) providing, on a display of the mobile computing device, the medication event outcome as feedback to the patient; and
   (10) storing the measured medication event outcome on the non-transitory computer readable storage medium on the mobile computing device.

2. The medication event logging method as set forth in claim 1, further comprising the steps of:
   (11) recording a third video activity of the patient speaking a few words or a sentence including audio information provided by audio sensors on the mobile computing device;
   (12) providing, on the display of the mobile computing device, instructions to capture the third video activity and audio information;
   (13) storing the audio information to the non-transitory computer readable storage medium on the mobile computing device;
   (14) processing, by the processor of the mobile computing device, the audio information including comparing it with predefined or iteratively adjusted parameters to generate a third medication event outcome; and
   (15) storing the third medication event outcome to a non-transitory computer readable storage medium on the mobile computing device,
wherein the medication event outcome is based on the third medication event outcome.

3. The medication event logging method as set forth in claim 1, further comprising the step of:
   (11) transmitting the medication event outcome to a storage and computing server.

4. A computer implemented automated intervention message construction and delivery method comprising the steps of:
   (1) recording video activity of a patient showing at least one pill on the palm of a patient's hand, or on a pill bottle cap with optically visible reference marks to optical sensors on a mobile computing device;

(2) providing, on a display of the mobile computing device, instructions to capture the video activity;

(3) storing the recording of the video activity to a non-transitory computer readable storage medium on the mobile computing device;

(4) employing a processor of the mobile computing device to process video activity to compare with predefined or iteratively adjusted parameters and generate a medication event outcome wherein the processor executes steps of:

(a) analyzing pill color including steps of:
  i. performing a color transformation of a respective image of a video sequence to provide a transformed image;
  ii. applying a pill color model to the transformed image;
  iii. calculating color match statistics; and (b) analyzing pill shape, including steps of:
  i. applying flood fill algorithms to the respective image based on the color match statistics;
  ii. applying a contour matching algorithm to a flooded region of the respective image;
  iii. matching geometrical shapes from a pill shape model to a respective contour to determine a best match shape;
  iv. computing shape dimensions of the best matched shape;
  v. comparing the shape dimensions to the pill shape model to provide a matched shape model; and
  vi. compare a pixel area overlapping the matched shape model and the flooded region to determine eligibility of the shape;

(c) analyzing pill size, including:
  i. identifying reference markers in the respective image;
  ii. estimating pill size based on the reference markers, a reference marker model and the matched shape model;
  iii. comparing estimated pill size with a pill size model;

(d) determining a pill identification outcome based on the analyzing of the pill color, pill shape and pill size;

(5) recording a second video activity showing the at least one pill in the mouth of the patient and the patient opening the mouth, the patient swallowing the at least one pill and then showing the mouth empty of the at least one pill to the optical sensors on the mobile computing device;

(6) providing, on a display of the mobile computing device, instructions to capture the second video activity;

(7) storing the recorded second video activity related to the patent's mouth to the non-transitory computer readable storage medium on the mobile computing device;

(8) determining, by the processor of the mobile computing device, a second medication event outcome based in the second video activity and predefined or iteratively adjusted parameters; and (9) storing the second medication event outcome to the non-transitory computer readable storage medium on the mobile computing device, wherein the medication event outcome is based on both the pill identification outcome and the second medication event outcome;

(10) providing, on a display of the mobile computing device, the medication event outcome as feedback to the patient;

(11) storing the medication event outcome on the non-transitory computer readable storage medium on the mobile computing device;

(12) receiving prior medication event outcomes associated with the patient;

(13) receiving medication prescription information of the patient;

(14) receiving a medication reminder schedule of the patient;

(15) employing a computer processor to compute adherence scores and patterns of the patient based at least on the medication event outcome and the medication reminder schedule; and

(16) storing adherence scores and patterns to the non-transitory computer readable storage medium.

5. The computer implemented automated intervention message construction and delivery method as set forth in claim 4, wherein adherence scores and patterns are numerical or categorical or combination thereof characterizing one or more of the patient's adherences to taking medication.

6. The computer implemented automated intervention message construction and delivery method as set forth in claim 4, further comprising the steps of:

(17) receiving a plurality of prior intervention messages delivered to a generic computer accessible by the patient;

(18) receiving the patient's engagement of the intervention messages;

(19) receiving the patient's adherence scores;

(20) employing the computer processor to compute intervention message engagement scores and patterns of the patient; and

(21) storing intervention message engagement scores and patterns to a non-transitory computer readable storage medium.

7. The computer implemented automated intervention message construction and delivery method as set forth in claim 6, wherein the patient's engagement with intervention messages includes computer recorded time spent in patient's viewing, interacting, and communicating with a generic computer having intervention messages on its video audio display.

8. The computer implemented automated intervention message construction and delivery method as set forth in claim 6, wherein the patient's engagement with intervention messages further includes text, images, video, or audio descriptions as intervention message feedback by the patient that can be stored on a non-transitory computer readable storage medium.

9. The computer implemented automated intervention message construction and delivery method as set forth in claim 6, wherein engagement scores and patterns are numerical or categorical or a combination thereof characterized by one or more of the patient's engagement with intervention messages.

10. The computer implemented automated intervention message construction and delivery method as set forth in claim 4, including a computer implemented medication experience data mining method comprising the steps of:

(aa) receiving patient's self-described medication experience that includes:
  a. a description of adverse reactions experienced by the patient;
  b. a description of patient's health, dietary and medication history of the patient;
  c. a description of adverse reaction remedial actions taken by the patient, and a description of outcomes of the remedial actions experienced by the patient; and
(bb) receiving medication label data published by medication manufacturer and regulatory authorities that includes:
  a. a pre-defined description of indications and contraindications of the medications;
  b. a pre-defined description of medication warnings and interactions; a pre-defined description of known adverse reactions; and
  c. a pre-defined description of remedial actions for known adverse reactions; receiving the patients' plurality of medication event outcome measures;
(cc) employing a computer processor to compute medication experience scores and patterns of the patient; and
(dd) storing medication experience scores and patterns to the non-transitory computer readable storage medium.

11. The method in claim 10, wherein medication experience scores and patterns are numerical or categorical or a combination thereof characterized by one or more of the patient's experience from taking medication.

12. The computer implemented automated intervention message construction and delivery method as set forth in claim 4, further including the steps of:
  (17) receiving the patient's engagement with interventions messages;
  (18) receiving the patient's adherence scores and patterns;
  (19) receiving patient's medication experience scores and patterns;
  (20) receiving a database of pre-defined reasons or explanations for not taking medications as prescribed;
  (21) receiving an adherence barrier likelihood of the patient for not taking medication;
  (22) receiving a plurality of patient's reasons or explanations for not taking medication as prescribed;
  (23) employing the computer processor to compute a revised adherence barrier likelihood of the patient; and
  (24) storing the revised adherence barrier likelihood to the non-transitory computer readable storage medium.

13. The computer implemented automated intervention message construction and delivery method as set forth in claim 12, wherein the adherence barrier likelihood is one or more numeric values indicating the likely reasons for the patient not taking medication.

14. The computer implemented automated intervention message construction and delivery method as set forth in claim 4, including a computer implemented intervention effectiveness analysis method comprising the steps of:
  (17) receiving the patient's adherence scores and patterns;
  (18) receiving the patient's intervention message engagement scores and patterns;
  (19) receiving the patient's medication experience scores and patterns;
  (20) employing the computer processor to compute intervention message content effectiveness of the patient; and
  (21) storing intervention message content effectiveness to the non-transitory computer readable storage medium.

15. The computer implemented automated intervention message construction and delivery method as set forth in claim 14, wherein intervention message content effectiveness is one or more numerical or categorical values or combination thereof indicating the effect of pre-defined message contents on change in one or more patient adherence scores and patterns.

16. The computer implemented automated intervention message construction and delivery method as set forth in claim 4, further including the steps of:
  (17) receiving adherence barrier likelihood;
  (18) receiving intervention message content effectiveness receiving patient's adherence scores and patterns;
  (19) receiving intervention message contents from a database of predefined intervention message contents;
  (20) employing a computer processor to compose intervention messages for a patient;
  (21) employing a computer processor to compute delivery conditions when messages or notice of messages are transmitted to the patient's mobile computing device that includes the date and time, or the generic location context, or combination of both; and
  (22) storing the intervention messages and their delivery conditions to the non-transitory computer readable storage medium.

17. The computer implemented automated intervention message construction and delivery method as set forth in claim 16, wherein an intervention message includes:
  a. one or more computer readable intervention message content including text, images, video, or audio descriptions that can be stored on the non-transitory computer readable storage medium, and provided on the video audio display of a generic computer; and
  b. one or more computer readable description of the reasons for intervention message including text, images, video, or audio descriptions that can be stored on a non-transitory computer readable storage medium, and provided on the video audio display of a generic computer.

18. The computer implemented automated intervention message construction and delivery method as set forth in claim 17, wherein intervention message content includes health encounter questions, tips, advices, suggestions, strategies, stories, scientific articles, examples, evidences in assisting the patient's adherence.

19. The computer implemented automated intervention message construction and delivery method as set forth in claim 17, wherein reasons for intervention message include description of patient's medication event outcome measures, patient's self-described medication experience, adherence scores and patterns, medication experience scores and patterns, intervention message engagement scores and patterns, and adherence barrier likelihood.

20. The computer implemented automated intervention message construction and delivery method as set forth in claim 4, wherein a computer implemented intervention message delivery method includes the steps of:
  (17) receiving intervention messages and intervention message delivery conditions;
  (18) receiving location information from the mobile computing device accessible to the patient to receive intervention messages; and
  (19) employing the computer processor to transmit intervention messages to the mobile computing device, the intervention message being accessible to the patient.

21. A system for assisting a patient with adherence to taking medication as prescribed, comprising:

(1) a mobile computing device including:
   a. first processor; and
   b. first memory operably connected to the first processor and including first processor executable code that when executed by the first processor performs steps of:
      i. recording video activity of patient showing at least one pill on the palm of a patient's hand, or on a pill bottle cap with optically visible reference marks to optical sensors on a mobile computing device;
      ii. providing, on a display of the mobile computing device, instructions to capture the video activity;
      iii. storing the recording of the video activity to a non-transitory computer readable storage medium on the mobile computing device;
      iv. processing the video sequences to compare with predefined or iteratively adjusted parameters and generate a medication event outcome including steps of:
         (a) analyzing pill color including steps of:
            i. performing a color transformation of a respective image; of a video sequence to provide a transformed image;
            ii. applying a pill color model to the transformed image; and
            iii. calculating color match statistics;
         (b) analyzing pill shape, including steps of:
            i. applying flood fill algorithms to the respective image based on the color match statistics;
            i. applying a contour matching algorithm to a flooded region of the respective image;
            ii. matching geometrical shapes from a pill shape model to a respective contour to determine a best match shape;
            iii. computing shape dimensions of the best matched shape;
            iv. comparing the shape dimensions to the pill shape model to provide a matched shape model; and
            v. comparing a pixel area overlapping the matched shape model and the flooded region to determine eligibility of the shape;
         (c) analyzing pill size, including:
            i. identifying reference markers in the respective image;
            ii. estimating pill size based on the reference markers, a reference marker model and the matched shape model;
            iii. comparing estimated pill size with a pill size model;
         (d) determining a pill identification outcome based on the analyzing of the pill color, pill shape and pill size;
      v. recording a second video activity showing the at least one pill in the mouth of the patient and the patient opening the mouth, the patient swallowing the at least one pill and then showing the mouth empty of the at least one pill to the optical sensors on the mobile computing device;
      vii. providing, on a display of the mobile computing device, instructions to capture the second video activity;
      viii. storing the recorded second video activity related to the patent's mouth to the non-transitory computer readable storage medium on the mobile computing device;
      ix. determining, by the processor of the mobile computing device, a second medication event outcome based in the second video activity and predefined or iteratively adjusted parameters; and
      x. storing the second medication event outcome to the non-transitory computer readable storage medium on the mobile computing device,
         wherein the medication event outcome is based on both the pill identification outcome and the second medication event outcome;
      xi. providing, on a display of the mobile computing device, the medication event outcome as feedback to the patient; and
      xii. storing the measured medication event outcome on the non-transitory computer readable storage medium on the mobile computing device;
(2) a computer system operably connected to the that includes:
   a. a second processor; and
   b. second memory operably connected to the second processor including second processor executable code that when executed by the second processor performs steps of:
      i. receiving the medication event outcome;
      ii. receiving medication prescription information of the patient;
      iii. receiving a medication reminder schedule of the patient;
      iv. receiving the intervention messages delivered to a mobile computing device accessible by the patient;
      v. receiving the patient's engagement of the intervention messages;
      vi. receiving patient's self-described medication experience;
      vii receiving medication label data;
      viii. receiving a database of pre-defined reasons or explanations for not taking medications as prescribed;
      ix. receiving a plurality of patient's reasons or explanations for not taking medication as prescribed;
      x. receiving intervention message contents from a database of predefined intervention message contents;
      xi. receiving location information from the mobile computing device accessible to the patient to receive intervention messages;
      xii. employing a computer processor to compose intervention messages for a patient;
      xiii. employing a computer processor to compute delivery conditions when messages or notice of messages are transmitted to the patient's mobile computing device that includes the date and time, or the generic location context, or combination of both;
      xiv. storing the intervention messages and their delivery conditions to the non-transitory computer readable storage medium; and
      xv. employing the computer processor to transmit intervention messages to the mobile computing device, the intervention message being accessible to the patient.

22. The system for assisting a patient with adherence to taking medication as set forth in claim 21, wherein the mobile computing device implemented system and the computer system transmit computer readable data between them, comprising:
   i. patient's medication event outcomes;
   ii. patient's self-described medication experiences;

iii. intervention messages;
iv. patient's engagement with interventions messages; and
v. location of the mobile computing device, while the patient interacts with mobile computing device implemented system.

\* \* \* \* \*